US011717659B2

(12) United States Patent
Kodama et al.

(10) Patent No.: US 11,717,659 B2
(45) Date of Patent: Aug. 8, 2023

(54) CELL TRANSPLANTATION DEVICE AND CELL TRANSPLANTATION UNIT

(71) Applicant: TOPPAN PRINTING CO., LTD., Taito-ku (JP)

(72) Inventors: Yoshihiro Kodama, Taito-ku (JP); Hiromitsu Kinoshita, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 535 days.

(21) Appl. No.: 16/832,260

(22) Filed: Mar. 27, 2020

(65) Prior Publication Data
US 2020/0222678 A1 Jul. 16, 2020

Related U.S. Application Data

(63) Continuation of application No. PCT/JP2018/013416, filed on Mar. 29, 2018.

(30) Foreign Application Priority Data

Sep. 29, 2017 (JP) .................................. 2017-190399

(51) Int. Cl.
*A61M 37/00* (2006.01)
*A61K 9/00* (2006.01)
(Continued)

(52) U.S. Cl.
CPC ....... *A61M 37/0015* (2013.01); *A61K 9/0021* (2013.01); *A61K 35/36* (2013.01); *A61P 17/14* (2018.01)

(58) Field of Classification Search
CPC ........ A61M 37/0015; A61M 2037/003; A61M 37/00; A61K 9/0021; A61K 35/36; A61P 17/14; C12M 33/04; C12M 33/06
See application file for complete search history.

(56) References Cited

U.S. PATENT DOCUMENTS 5,417,683 A * 5/1995 Shiao ...................... A61F 2/10
606/1
5,868,758 A * 2/1999 Markman .......... A61B 17/3468
606/187
(Continued)

FOREIGN PATENT DOCUMENTS

JP 2002-505605 A 2/2002
JP 2003-506130 A 2/2003
(Continued)

OTHER PUBLICATIONS

Japanese Office Action dated Oct. 26, 2021 in Japanese Patent Application No. 2019-181436 (with English translation), 5 pages.
(Continued)

*Primary Examiner* — Amber R Stiles
(74) *Attorney, Agent, or Firm* — Oblon, McClelland, Maier & Neustadt, L.L.P.

(57) ABSTRACT

A cell transplantation device for placing a cell group at a target region in at least one of an intradermal layer and a subcutaneous layer in a living body, including a device body including a protruding portion having an accommodating portion for accommodating a liquid composition including the cell group. The protruding portion has an opening that communicates with the accommodating portion, and the protruding portion penetrates a skin surface of the living body such that the opening of the protruding portion reaches the at least one of the intradermal layer and the subcutaneous layer and that the cell group accommodated in the accommodating portion is placed at the target region through the opening.

20 Claims, 18 Drawing Sheets

(51) Int. Cl.
*A61K 35/36* (2015.01)
*A61P 17/14* (2006.01)

(56) References Cited

U.S. PATENT DOCUMENTS

| | | | |
|---|---|---|---|
| 2005/0244385 A1 | 11/2005 | Brittingham et al. | |
| 2013/0041265 A1 | 2/2013 | Sostek et al. | |
| 2014/0037592 A1 | 2/2014 | Toyoshima et al. | |
| 2017/0368322 A1 | 12/2017 | Kato et al. | |

FOREIGN PATENT DOCUMENTS

| | | |
|---|---|---|
| JP | 2008-029331 A | 2/2008 |
| JP | 2013-13668 A | 1/2013 |
| JP | 2013-526300 A | 6/2013 |
| JP | 2013-202016 A | 10/2013 |
| JP | 2015-171381 A | 10/2015 |
| JP | 2017-023059 A | 2/2017 |
| JP | 2017-158442 A | 9/2017 |
| WO | 2006-516006 A | 6/2006 |
| WO | WO 2007/042818 A1 | 4/2007 |
| WO | WO 2011/140497 A2 | 11/2011 |
| WO | WO2012/108069 A1 | 8/2012 |
| WO | WO 2016/147476 A1 | 9/2016 |
| WO | WO2017/073625 A1 | 5/2017 |
| WO | WO2017/135060 A1 | 8/2017 |

OTHER PUBLICATIONS

Extended European Search Report dated Oct. 20, 2020 in European Patent Application No. 18861039.8, 7 pages.
International Search Report dated Jun. 12, 2018 in PCT/JP2018/013416, filed Mar. 29, 2018, (with English Translation).
Office Action dated May 28, 2019 in Japanese Patent Application No. 2019-077904, filed Apr. 16, 2019, (with English Translation).
Japanese Office Action dated Apr. 26, 2022 in Japanese Patent Application No. 2019-181436 (with unedited computer generated English translation), 7 pages.

* cited by examiner

CELL TRANSPLANTATION DEVICE AND CELL TRANSPLANTATION UNIT

CROSS-REFERENCE TO RELATED APPLICATIONS

The present application is a continuation of International Application No. PCT/JP2018/013416, filed Mar. 29, 2018, which is based upon and claims the benefits of priority to Japanese Application No. 2017-190399, filed Sep. 29, 2017. The entire contents of all of the above applications are incorporated herein by reference.

BACKGROUND OF THE INVENTION

Field of the Invention

The present invention relates to a cell transplantation device and a cell transplantation unit for use in transplantation of cells into a skin region.

Discussion of the Background

Techniques have been developed for transplanting cell groups obtained by culturing cells collected from a living body into the intradermal layer or subcutaneous layer in a living body. For example, regeneration of hair has been performed by purifying cell groups that contribute to formation of hair follicles, which are organs that produce hair, and transplanting the cell groups into intradermal sites.

Hair follicles are formed by interactions between epithelial cells and mesenchymal cells. For good hair regeneration, it is desired that the cell groups transplanted become hair follicles having a normal structure and good hair formation ability. Therefore, various research and development projects have been performed for methods of producing cell groups that can produce hair follicles (for example, see PTLs 1 to 3).

PTL 1: WO2017/073625
PTL 2: WO2012/108069
PTL 3: JP 2008-29331 A

SUMMARY OF THE INVENTION

According to an aspect of the present invention, a cell transplantation device for placing a cell group at a target region in at least one of an intradermal layer and a subcutaneous layer in a living body, includes a device body including a protruding portion having an accommodating portion for accommodating a liquid composition including the cell group. The protruding portion has an opening that communicates with the accommodating portion, and the protruding portion penetrates a skin surface of the living body such that the opening of the protruding portion reaches the at least one of the intradermal layer and the subcutaneous layer and that the cell group accommodated in the accommodating portion is placed at the target region through the opening.

According to another aspect of the present invention, a cell transplantation apparatus includes a tray having at least one placement region for holding a liquid composition including a cell group to be transferred, and a cell transplantation device that transfers the cell group from the tray to a target region in at least one of an intradermal layer and a subcutaneous layer in a living body. The cell transplantation device includes a device body including a protruding portion having at least one accommodating portion for accommodating the liquid composition including the cell group taken from the placement region, the at least one accommodating portion is respectively assigned to the at least one placement region, the protruding portion has an opening that communicates with the accommodating portion, and the protruding portion penetrates a skin surface of the living body such that the opening of the protruding portion reaches the at least one of the intradermal layer and the subcutaneous layer and that the cell group accommodated in the accommodating portion is placed at the target region through the opening.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
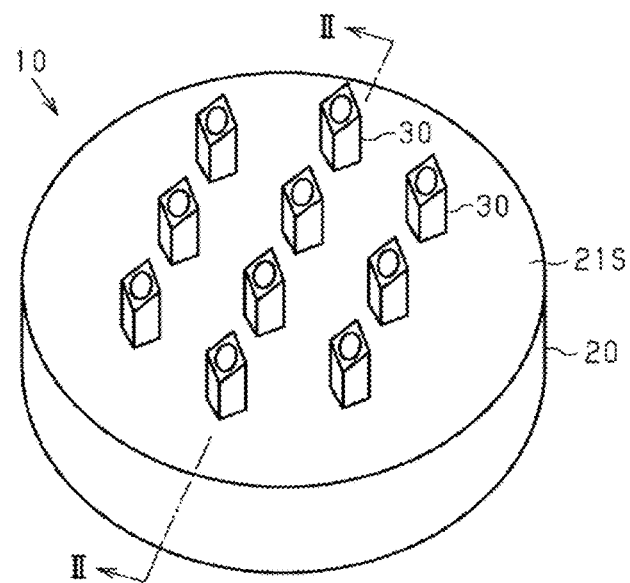
FIG. 1 is a view illustrating a perspective structure of a cell transplantation device in an embodiment of a cell transplantation device.

The embodiments will now be described with reference to the accompanying drawings, wherein like reference numerals designate corresponding or identical elements throughout the various drawings.

With reference to FIGS. 1 to 40, an embodiment of a cell transplantation device used for cell transplantation, and a cell transplantation unit including the cell transplantation device will be described.

<Object to be Transplanted>

A cell transplantation device of the present embodiment is used for transplanting a cell group to at least one of the intradermal layer and subcutaneous layer in a living body. First, a cell group to be transplanted will be described.

The cell group to be transplanted includes a plurality of cells. The cell group may be an aggregate of a plurality of cells that are aggregated, or may be an aggregate of a plurality of cells that are joined by intercellular junctions. Alternatively, the cell group may be composed of a plurality of dispersed cells. Further, cells included in the cell group may be undifferentiated cells, or may be cells that have been differentiated. The cell group may also include both undifferentiated cells and differentiated cells. The cell group includes, for example, masses of cells (spheroids), primordia, tissues, organs, organoids, and mini organs.

The cell group has an ability to control tissue formation in a living body when placed in the intradermal or subcutaneous layer. In the present embodiment, the description will be given of an example in which the object to be transplanted is a cell group that contributes to hair growth or hair restoration. For example, such a cell group has an ability to function as a hair follicle organ, an ability to differentiate into a hair follicle organ, an ability to induce or promote formation of a hair follicle organ, or an ability to induce or promote formation of hair in a hair follicle. Further, the cell group may include cells that contribute to control of hair color, such as pigment cells or stem cells that differentiate into pigment cells. Further, the cell group may also include vascular cells.

Specifically, an example of the cell group to be transplanted in the present embodiment is a hair follicle primordium, which is a primitive hair follicle organ. The hair follicle primordium includes mesenchymal cells and epithelial cells. In the hair follicle organ, dermal papilla cells, which are mesenchymal cells, induce differentiation of hair follicle epithelial stem cells to form a hair bulb, and hair matrix cells in the hair bulb repeat division to form a hair. The hair follicle primordium is a cell group that differentiates into such hair follicle organs.

The hair follicle primordium is formed, for example, by culturing a mixture of mesenchymal cells derived from mesenchymal tissues such as dermal papilla and epithelial cells derived from epithelial tissues located in a bulge region or a hair bulb base under predetermined conditions. It should be noted that the process of forming hair follicle primordia is not limited to the above example. In addition, the mesenchymal cells and epithelial cells used for formation of hair follicle primordia may also be derived from any tissue. These cells may be derived from a hair follicle organ, may be derived from an organ different from the hair follicle organ, or may be derived from a pluripotent stem cell.

<Cell Transplantation Device>

A cell transplantation device of the present embodiment will be described. First, with reference to FIG. 1, a basic configuration of a cell transplantation device will be described.

As shown in FIG. 1, a cell transplantation device 10 includes one substrate 20 and one or more projections 30. The substrate 20 includes a substrate surface 21S, and the projections 30 protrude from the substrate surface 21S. In other words, the substrate surface 21S supports a proximal end of the projections 30. In the following description, a thickness direction of the substrate 20, that is, a direction in which the substrate 20 and the projection 30 are disposed is referred to as a first direction, and any direction extending in a plane perpendicular to the first direction is referred to as a second direction. When the substrate surface 21S is a flat surface, the second direction is a direction extending along the substrate surface 21S.

The cell transplantation device 10 includes a portion that functions as an accommodating portion for accommodating a cell group, and a portion that functions as a penetrating portion configured to be advanced toward a target region via a skin surface, which is a region to be transplanted with a cell group. The penetrating portion has an opening which serves as an outlet for a cell group. The opening is placed at a target region when the penetrating portion penetrates the skin. The target region is at least one of the intradermal layer and subcutaneous layer. In addition, the cell transplantation device 10 preferably includes a portion that functions as a placement assisting portion for assisting placement of a cell group into the target region.

A method for transplanting cells by using the cell transplantation device 10 includes: an accommodating step of accommodating a liquid material containing a cell group into an accommodating portion; a penetration step of advancing a penetrating portion toward a target region via a skin surface; and a placement step of placing a cell group into a target region through an opening of the penetrating portion.

Hereinafter, the description will be given of the detailed configurations of the accommodating portion, the penetrating portion, and the placement assisting portion, and the details of the accommodating step, the penetration step, and the placement step.

<Accommodating Portion and Accommodating Step>

The accommodating portion accommodates a liquid material which contains a cell group and a storage liquid, which is liquid that protects the cell group. In the accommodating portion, the cell group is held in the storage liquid. The storage liquid may be any liquid that is unlikely to hinder the viability of cells, and is preferably a liquid that has a small influence on a living body when injected into the living body. For example, the storage liquid is preferably a physiological saline. The storage liquid may contain, in addition to the physiological saline, additive components such as a nutrient composition. Alternatively, the storage liquid may be a medium for cell culture. When the medium has a composition that is not suitable for injection into a living body, the storage liquid, or the medium, is preferably replaced with a liquid such as a physiological saline, which has minimal influence on the living body, before a cell group is injected into the living body. In addition, the replacing liquid is not limited to a physiological saline. Examples of the replacing liquid include a liquid that protects the skin, such as petrolatum or lotion, and a liquid in which such liquids and a physiological saline are mixed.

The above liquid material which contains the cell group and the storage liquid may be a low viscosity fluid or a high viscosity fluid. Further, the above liquid material may be a sol or a gel. The above liquid material may have a configuration in which a cell group and a storage liquid are held in a matrix made of a polymer material or the like. Examples of the polymer material constituting the matrix include, but are not limited to, collagen and hyaluronic acid.

In one form of the accommodating portion, the projection 30 functions as an accommodating portion.

Figure 2:
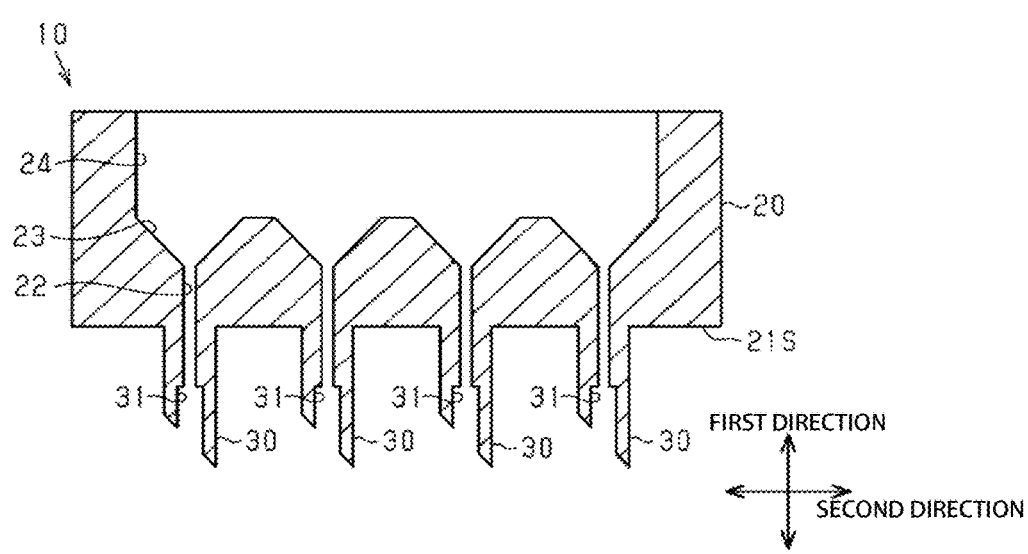
FIG. 2 is a cross-sectional view illustrating a cross-sectional structure of a cell transplantation device of an embodiment, taken along the line II-II of FIG. 1.

As shown in FIG. 2, the projection 30 is a structure having an internal channel 31 that defines a space inside the projection 30. The internal channel 31 accommodates a cell group. When one cell group is an aggregate of a set of cells, each projection 30 is preferably configured to accommodate one cell group. That is, each projection 30 preferably has the internal channel 31 of a size suitable for accommodating one cell group. Specifically, when the cell group is a group of hair follicle primordia, the internal channel 31 of the projection 30 preferably has a size suitable for accommodating one group of hair follicle primordia.

When the cell transplantation device 10 includes a plurality of projections 30, each of the plurality of projections 30 functions as an accommodating portion. That is, the cell transplantation device 10 includes the accommodating portions for the respective projections 30. Each of the plurality of projections 30 preferably has a structure that accommodates a predetermined number of cell groups. Preferably, each projection 30 is configured to accommodate one cell group. For example, it is preferred that the plurality of projections 30 have the same size of the internal channels 31 defined by the respective projections 30, and the size of each internal channel 31 in the projection 30 is suitable for accommodating one cell group.

Figure 3:
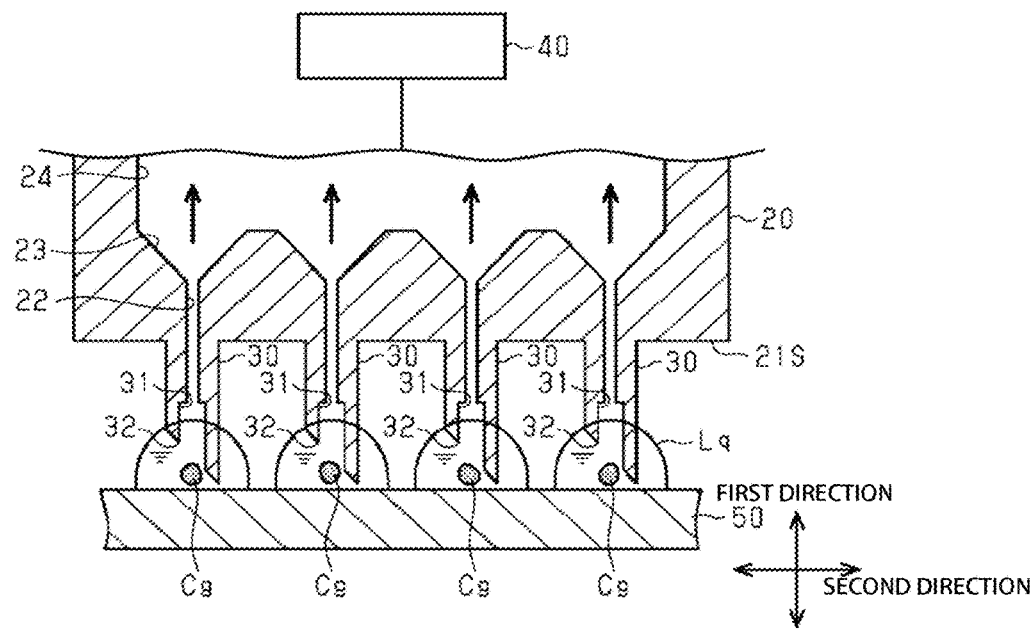
FIG. 3 is a view illustrating an example of a step of accommodating cell groups by using a cell transplantation device of an embodiment.

As shown in FIG. 3, the cell transplantation device 10 is configured to take cell groups Cg placed in a tray 50 such as a culture container outside the cell transplantation device 10 into the projections 30. The following description will be given of one form, in which the cell transplantation device 10 takes the cell groups Cg into the projections 30 from the distal end region of the projections 30, and the accommodating step in such a form.

The internal channel 31 of the projection 30 extends therethrough in the first direction from the proximal end to the distal end of the projection 30. One end of the internal channel 31 in the extending direction thereof reaches the peripheral surface of the projection 30 at the distal end region of the projection 30 and forms the opening 32, whereas the other end in the extending direction of the internal channel 31 reaches the substrate 20. That is, a space defined by the internal channel 31 communicates with a space outside the cell transplantation device 10 via the opening 32 of the projection 30 and also communicates with a space inside the substrate 20.

Further, the internal channel 31 may generally extend in a straight shape or in a curved shape as long as it extends from the proximal end of the projection 30 and is open to the distal end region of the projection 30.

In the accommodating step, the cell transplantation device 10 takes the cell group Cg via the opening 32 into the internal channel 31. More specifically, the distal end region including the opening 32 of the projection 30 is directed to a portion where the cell group Cg together with the protective liquid Lq is located in the tray 50 so that the cell group Cg together with the protective liquid Lq is taken into the internal channel 31.

For example, the cell transplantation device 10 uses a capillary phenomenon by which the liquid material which contains the protective liquid Lq and the cell group Cg is drawn up through the internal channel 31 to thereby accommodate the cell group Cg.

When a capillary phenomenon is used, an internal diameter of the internal channel 31 is designed taking into consideration the type of the protective liquid Lq, the material of the projection 30, and the like, to induce a capillary phenomenon of the liquid material which contains the protective liquid Lq and the cell group Cg.

For example, the cell transplantation device 10 may include an induction unit 40 having a structure for taking in the cell group Cg. For example, the induction unit 40 includes a suction mechanism or a suction structure having a piston or the like so that gas or liquid in the internal channel 31 is suctioned from an end on which the opening 32 is not provided. The cell transplantation device 10 suctions the cell group Cg together with the protective liquid Lq into the internal channel 31 by suction performed by the induction unit 40 to thereby accommodate the cell group Cg.

In another example, the induction unit 40 includes a mechanism that generates an electroosmotic flow in response to application of a voltage. The cell transplantation device 10 uses the electroosmotic flow to generate a flow in the liquid material containing the protective liquid Lq and the cell group Cg so that the cell group Cg together with the protective liquid Lq flows into the internal channel 31. Thus, the cell group Cg is accommodated in the projection 30.

Further, the cell transplantation device 10 may also take the cell group Cg into the internal channel 31 by a combination of two or more of a capillary phenomenon, suction, and electroosmotic flow.

When the cell transplantation device 10 includes the plurality of projections 30, it is time-consuming to repeat accommodation of the cell group Cg into the projection 30 for each of the projections 30. According to the form illustrated above, the cell groups Cg can be collectively accommodated into the plurality of projections 30. Thus, efficiency in accommodation of the cell groups Cg can be improved.

As described above, in the form in which the projection 30 functions as the accommodating portion, it is preferred that the cell transplantation device 10 includes a plurality of accommodating portions and the cell groups Cg are accommodated in the respective accommodating portions. The cell transplantation device 10 is preferably configured to take the cell groups Cg placed in the tray 50 into each of the plurality of accommodating portions in one operation. Further, for the cell groups Cg, which are hair follicle primordia, it is preferred that each hair follicle primordium is separated from others when placed in the tray 50.

Further, the internal structure of the substrate 20 is not specifically limited as long as it includes a flow path for allowing a fluid to flow out of the internal channel 31 of the projection 30 and allowing a fluid to flow into the internal channel 31. FIGS. 2 and 3 illustrate that the substrate 20 includes a set of a proximal flow path 22 extending from the substrate surface 21S in a direction away from the projection 30 and an intermediate flow path 23 connecting to the proximal flow path 22, each corresponding to the respective projections 30. The proximal flow path 22 communicates with the internal channel 31, and the intermediate flow path 23 has an internal diameter gradually increasing from the proximal flow path 22 toward the end away from the substrate surface 21S. Further, the substrate 20 includes one common flow path 24, which communicates with all the intermediate flow paths 23. The fluid flowing out from the internal channel 31 flows, in sequence, through the proximal flow path 22, the intermediate flow path 23, and the common flow path 24. The fluid flowing toward the internal channel 31 flows, in sequence, the common flow path 24, the intermediate flow path 23, and the proximal flow path 22. Although the intermediate flow path 23 may not be necessarily provided, the intermediate flow path 23 facilitates a flow of fluid toward the internal channel 31 since the internal diameter of the flow path gradually decreases toward the internal channel 31.

Figure 4:
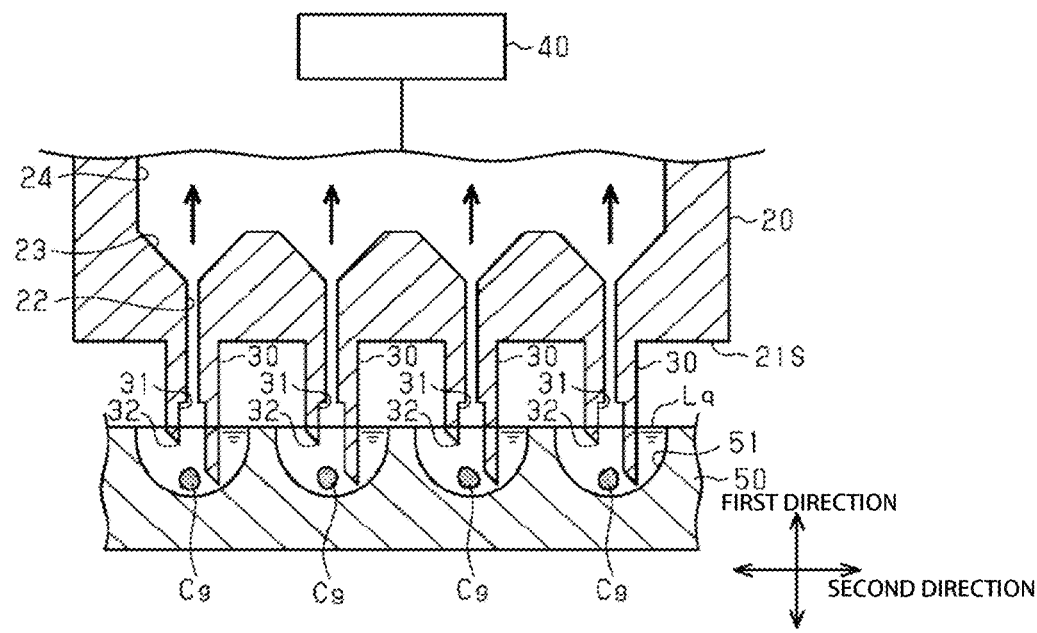
FIG. 4 is a view illustrating another example of placement of cell groups in a tray in a step of accommodating cell groups by using a cell transplantation device of an embodiment.
Figure 5:
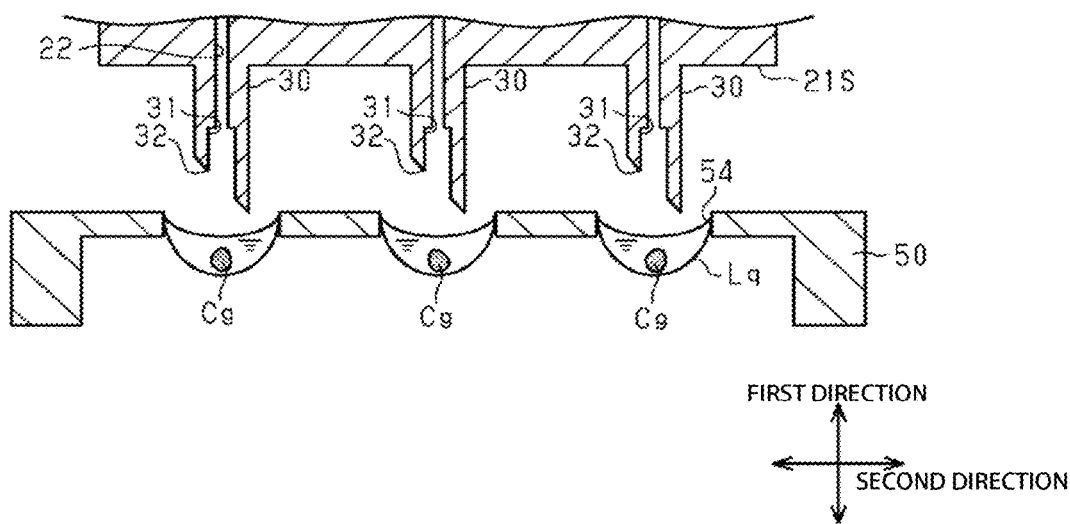
FIG. 5 is a view illustrating another example of placement of cell groups in a tray in a step of accommodating cell groups by using a cell transplantation device of an embodiment.

Further, although FIG. 3 illustrates that the liquid material containing the protective liquid Lq and the cell group Cg is placed on a plane of the tray 50, placement of the liquid material in the tray 50 is not limited thereto. For example, as shown in FIG. 4, the liquid material may be placed in a recess 51 of the tray 50. Alternatively, as shown in FIG. 5, the liquid material may be retained inside and around the through hole 54 of the tray 50.

As described above, the internal channel 31 communicates with the inside of the substrate 20 on an end away from the opening 32. For this reason, the projection 30 preferably has a configuration for retaining the cell group Cg inside the projection 30.

Figure 6:
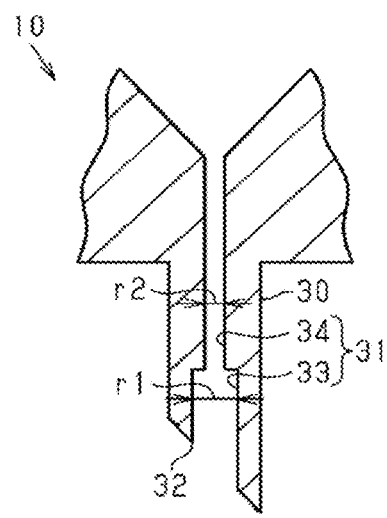
FIG. 6 is an enlarged view illustrating a cross-sectional structure of a projection in a cell transplantation device of an embodiment.

For example, as shown in FIGS. 2 to 5, the internal diameter of the internal channel 31 preferably varies in the projection 30. Specifically, as shown in FIG. 6, the internal channel 31 is a multi-stage hole, and has a large diameter portion 33 having a first internal diameter r1 and a small diameter portion 34 having a second internal diameter r2, which is smaller than the first internal diameter r1. In other words, a cross-sectional area of the flow path of the small diameter portion 34 is smaller than a cross-sectional area of the flow path of the large diameter portion 33. The large diameter portion 33 is located on a side closer to the distal end of the projection 30 than the small diameter portion 34 is. The opening 32 forms an end of the large diameter portion 33, and is included in the large diameter portion 33.

The first internal diameter r1 has a size that allows the cell group Cg to pass through the large diameter portion 33, and the second internal diameter r2 has a size that does not allow the cell group Cg to pass through the small diameter portion 34. For example, the first internal diameter r1 is larger than the size assumed as the maximum diameter of the cell group Cg, and the second internal diameter r2 is smaller than the size assumed as the minimum diameter of the cell group Cg.

With this configuration, the cell group Cg entering the internal channel 31 via the opening 32 passes through the large diameter portion 33 along with a flow of the protective liquid Lq. Then, the cell group Cg is retained in the large diameter portion 33 without entering the small diameter portion 34, although the protective liquid Lq flows into the small diameter portion 34. Therefore, the cell group Cg can be retained inside the projection 30. Even when the cell groups Cg are collectively accommodated in the plurality of projections 30, each cell group Cg can be accommodated in the respective projections 30. Further, in retaining the cell group Cg inside the projection 30, the protective liquid Lq is preferably present on a periphery of the cell group Cg. Preferably, the cell transplantation device 10 has a configuration in which the protective liquid Lq can be present on the periphery of the cell group Cg when the cell group Cg is retained inside the projection 30. The protective liquid Lq present on the periphery of the cell group Cg can prevent the cell group Cg from becoming dried. By preventing the cell group Cg from becoming dried, alteration of the cell group Cg can be reduced, which reduces adhesion of the cell group Cg to the inside of the projection 30.

The above description illustrates the internal channel 31 whose internal diameter changes in two stages, that is, the first internal diameter r1 and the second internal diameter r2. However, the internal diameter of the internal channel 31 in the projection 30 is not limited to the above shape, and may change in three or more stages, or may gradually change. In other words, in the internal channel 31, the second portion having the cross-sectional area of the flow path, which is smaller than that of the first portion having the opening 32, may be located at a position closer to the proximal end of the projection 30 than the first portion is.

Further, instead of the internal channel 31 having the multi-stage hole, a filter that allows the protective liquid Lq to pass through and does not allow the cell group Cg to pass through may be provided in the internal channel 31. In this configuration as well, the cell group Cg can be retained inside the projection 30. Further, the filter may also be provided in the internal channel 31, which has the multi-stage hole. In addition, the cell groups Cg can also be retained in the projections 30 by adjusting a magnitude of the force suctioning the liquid material containing the cell group Cg and the protective liquid Lq or by adjusting a fluidity of the liquid material.

The protective liquid Lq taken into the internal channel 31 together with the cell group Cg from the tray 50 may be a storage liquid, or may be a liquid different from a storage liquid, which is replaced with a storage liquid after the liquid is taken into the internal channel 31.

For example, the cell groups Cg are cultured in the tray 50, and the medium is then replaced with a physiological saline in the tray 50. Subsequently, the cell transplantation device 10 takes the protective liquid Lq, which is a physiological saline, and the cell group Cg into the internal channel 31. In this case, the protective liquid Lq is a storage liquid.

Alternatively, the cell groups Cg may be cultured in the tray 50, and then the cell transplantation device 10 takes the protective liquid Lq, which is the medium, together with the cell groups Cg into the internal channel 31. After the cell groups Cg are taken into the internal channel 31, the protective liquid Lq, which is the medium, is partially or entirely suctioned in a direction away from the opening 32 of the internal channel 31 and externally discharged. Suctioning of the protective liquid Lq may also serve as suctioning to take in the cell group Cg. Alternatively, an absorbent may be provided inside the substrate 20 so that the protective liquid Lq in the internal channel 31 is absorbed by the absorbent. Examples of the absorbent include a porous body such as sponge. After the protective liquid Lq is discharged, a storage liquid such as a physiological saline is injected into the internal channel 31 from an end which does not have the opening 32, or from the opening 32.

Further, when the medium is used as a storage liquid, the protective liquid Lq, which is the medium, is taken into the internal channel 31 together with the cell group Cg, and the medium which has been taken in functions as a storage liquid. Moreover, after the medium which has been taken in temporarily functions as a storage liquid, the medium as the storage liquid may be replaced with a liquid such as a physiological saline in the cell transplantation device 10. The replacing liquid is not limited to a physiological saline, and may also be a liquid that protects the skin, such as petrolatum or lotion, or a liquid in which such liquids and a physiological saline are mixed. The storage liquid is replaced, for example, by suctioning the storage liquid in the internal channel 31 from an end which does not have the opening 32, and then injecting a new storage liquid into the internal channel 31 from the end which does not have the opening 32, or from the opening 32.

When a new storage liquid is injected from the end which does not have the opening 32 into the internal channel 31 for replacement with the protective liquid Lq or for replacement with the storage liquid, the cell transplantation device 10 can be provided with an injection unit that injects a storage liquid into the internal channel 31 from the end which does not have the opening 32. Alternatively, the storage liquid can be supplied to the internal channel 31 via the opening 32 by means of suction. When the cell transplantation device 10 is configured to be capable of replacing the liquid inside the internal channel 31, and perform replacement between the protective liquid Lq and a storage liquid in accommodation of the cell groups Cg, the medium around the cell group Cg can be efficiently replaced by a storage liquid.

The above form in which the projection 30 functions as the accommodating portion is described as being preferable when each cell group Cg is accommodated in a respective accommodating portion. However, two or more cell groups Cg can also be accommodated in each accommodating portion. Moreover, in the above form, the cell group Cg placed in one of a plurality of regions separated from each other in the tray 50 is taken into one projection 30. However, the cell groups Cg collectively placed in a common region in the tray 50 can be taken into a plurality of projections 30. Further, the cell transplantation device 10 may also take the cell group Cg into the projection 30 via an internal flow path of the substrate 20 instead of the distal region of the projection 30. That is, the cell group Cg may also be introduced into the internal channel 31 from the end which does not have the opening 32.

In another form of the accommodating portion, the substrate 20 may function as the accommodating portion. That is, the cell group Cg is accommodated in an internal space of the substrate 20. The inside of the substrate 20 may be partitioned into a plurality of regions so that a predetermined amount of cell groups Cg is accommodated in each region. Alternatively, a plurality of cell groups Cg may be collectively accommodated in one region which does not have a partition. The cell group Cg may be introduced into the substrate 20 through the inside of the projection 30 from the distal region of the projection 30 and accommodated in the substrate 20. Alternatively, the cell group Cg may be introduced into the substrate 20 from a portion of the substrate 20 on a side opposite to that facing the projection 30. In addition, a culture container in which the cell group Cg is cultured may also be assembled in the substrate 20 so that the substrate 20 accommodates the cell group Cg together with the culture container. In still another form of the accommodating portion, the projection 30 and the substrate 20 may function as the accommodating portion.

Further, instead of the cell transplantation device 10 taking the cell group Cg from the outside into the accommodating portion, the cell group Cg can be cultured in the accommodating portion, that is, inside the projection 30 or inside the substrate 20. For example, the cell transplantation device 10 can be placed with the opening 32 of the projection 30 oriented upward so that the inside of the projection 30, which is the accommodating portion, can be used as a region in which cells are cultured. In this case, since the process of accommodating the cell groups Cg in the accommodating portion during transplantation is not necessary, the efficiency of work required for cell transplantation can be further increased.

When the cell transplantation device 10 takes in the cell groups Cg into the accommodating portion, it is necessary to align the cell transplantation device 10 and the cell groups Cg, that is, align the cell transplantation device 10 and the tray 50. In order to achieve alignment, either or both of the cell transplantation device 10 and the tray 50 may include an alignment unit. The alignment unit, as described later, can be embodied as a configuration in which positions of the cell transplantation device 10 and the tray 50 can be controlled by using their outer shapes, or can be embodied as a camera or a robot mechanism.

<Penetrating Portion, Penetration Step, and Placement Step>

The projection 30 also serves as a penetrating portion. The penetrating portion is configured to be advanced toward the target region via a skin surface. In other words, the projection 30 which functions as a penetrating portion is configured to puncture the skin.

The shape of the projection 30 is not specifically limited as long as it can puncture the skin. The projection 30 may have a conical or pyramid shape, or may have a cylindrical or prismatic shape. Alternatively, the projection 30 may have a shape formed by connecting the bottom of a cone or pyramid to the top of a cylinder or prism, or a shape formed by truncating a prismatic or cylindrical shape obliquely relative to the extending direction thereof, or a shape formed by truncating the structure, which is formed by connecting the bottom of a cone or pyramid to the top of a cylinder or prism, obliquely relative to the extending direction thereof.

Figure 7:
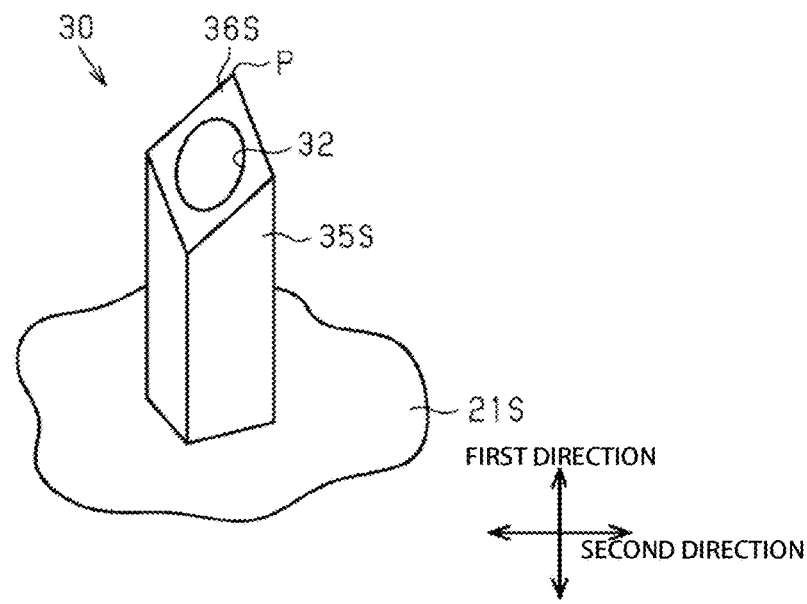
FIG. 7 is an enlarged view illustrating a perspective structure of a projection in a cell transplantation device of an embodiment.

FIG. 7 illustrates an exemplary shape of the projection 30. In the example shown in FIG. 7, the projection 30 has a shape of a quadrangular prism truncated obliquely relative to the extending direction thereof. The projection 30 has lateral faces 35S extending in a first direction from a rectangular bottom face, which is defined on the substrate surface 21S, and a top face 36S, which is inclined relative to the bottom face. The side surfaces 35S and the top face 36S form the peripheral surface of the projection 30. The sides of the top face 36S are all inclined relative to the bottom face, and edge of the projection 30 from the substrate surface 21S to one of the vertices of the top face 36T has the largest length. The point on the vertex at which the length of the projection 30 becomes largest is an apex P, and the apex P is located on the edge of the projection 30 when viewed in the first direction.

The top face 36S has the opening 32. The opening 32 functions as an intake of the accommodating portion for taking the cell group Cg into the accommodating portion, and also functions as an outlet of the penetrating portion for releasing the cell group Cg.

In the example shown in FIG. 7, the width of the projection 30 in the second direction is constant from the proximal end of the projection 30 and decreases toward the apex in the distal region of the projection 30. The shape is merely an example, and the width of the projection 30 in the second direction may also gradually decrease from the proximal end to the distal end. Further, the side surface 35S and the top 36S may also be a curved face.

In the configuration in which the projection 30 has the top face 36S in which the opening 32 is provided and the apex P is located on the edge of the projection 30, the following effects are obtained. That is, since the distal region has a shape pointed toward one apex P, the ease of puncture by the projection 30 into the skin is increased. Further, since the apex P is located on the edge of the projection 30, a large region can be ensured in the region excluding the apex P to adjust the size and position of the opening 32.

Further, when the internal channel 31 is bent inside the projection 30, the opening 32 can be provided on the side surface 35S. Alternatively, the projection 30 may not necessarily have the top face 36S and the apex P. For example, the projection 30 may have a shape in which the internal channel 31 extends through the center of the cone, that is, the width of the projection 30 decreases toward the opening 32 at the center of the projection 30, and the opening 32 is located at the most distal end of the projection 30.

Further, the shape of the projection 30 is not limited to a needle shape, that is, a shape in which the length in the first direction is longer than the length in the second direction. The shape of the projection 30 may be a blade-shape, that is, a linear shape in which the length in the extending direction, which is one of the second directions, is longer than the length in the first direction, and a distal portion of the projection 30 extends in a direction different from the first direction, for example, along the extending direction. For example, the projection 30 may be formed as a triangular prism shape that extends along the extending direction while one of three rectangular side surfaces of the triangular prism is in contact with the substrate 20, and a side of the triangular prism shared by the other two side surfaces serves as the tip of the projection 30.

Alternatively, a portion which functions as a blade for cutting the skin may be provided in a distal region of the projection 30 so as to protrude from the other portion of the projection 30.

Figure 8:
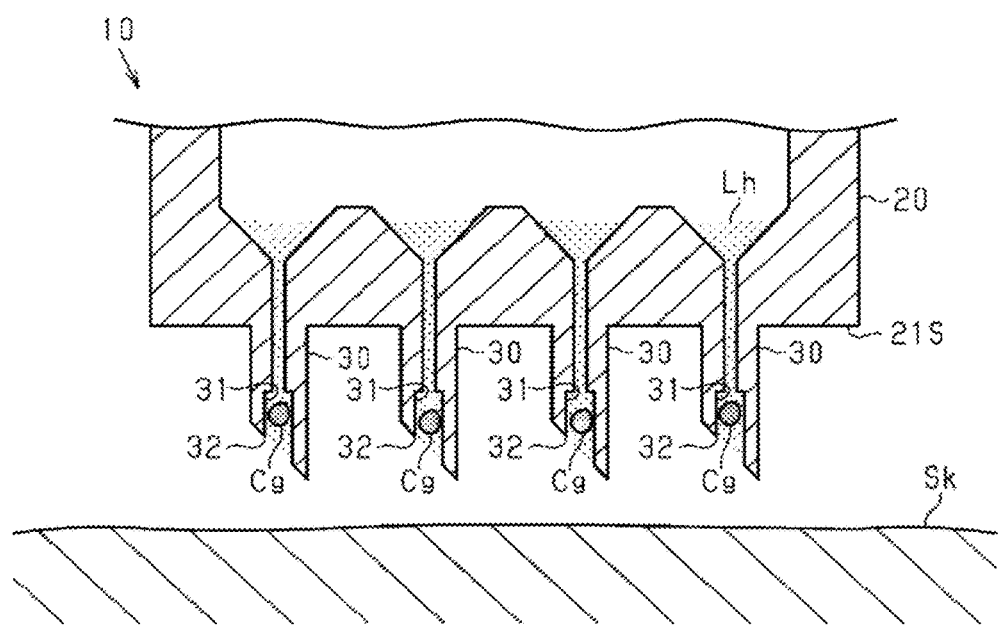
FIG. 8 is a view illustrating an example of placement of a cell transplantation device when a penetration step of cell groups is performed by using a cell transplantation device of an embodiment.
Figure 9:
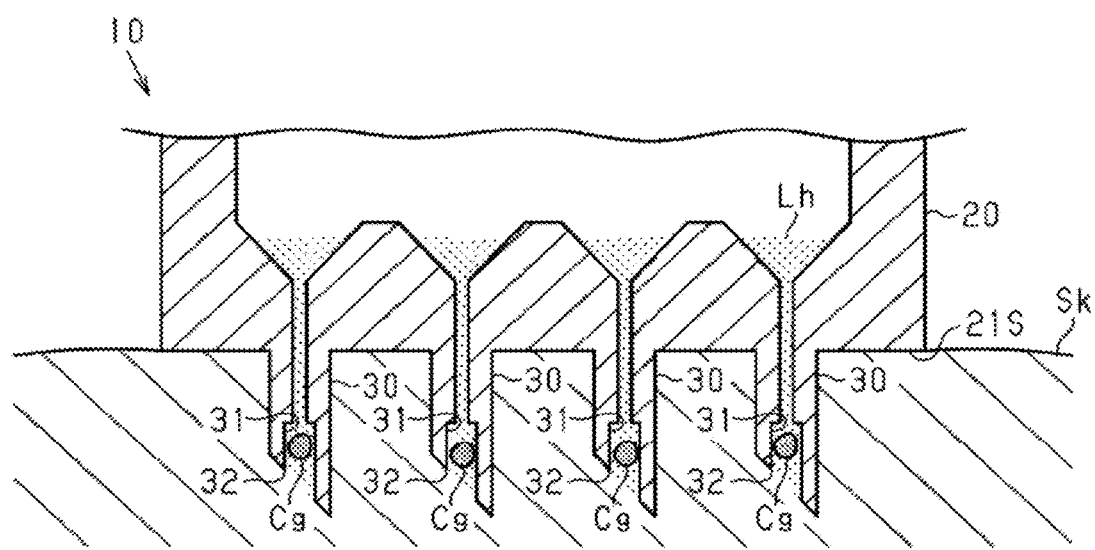
FIG. 9 is a view illustrating an example of a penetration step of cell groups by using a cell transplantation device of an embodiment.
Figure 10:
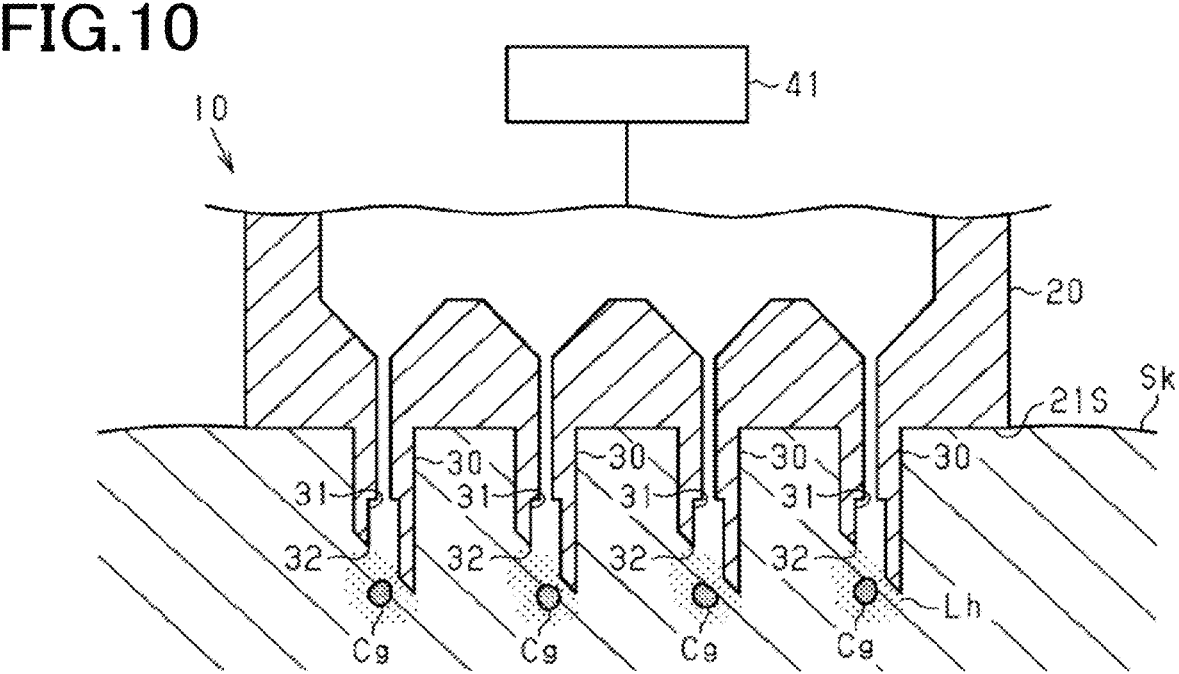
FIG. 10 is a view illustrating an example of a placement step of cell groups by using a cell transplantation device of an embodiment.

With reference to FIGS. 8 to 10, the penetration step and the placement step will now be described. In FIGS. 8 to 10, a process of accommodating the cell groups Cg in the projection 30, which functions as the accommodating portion, and then placing the cell groups Cg in the target region will be described.

As shown in FIG. 8, the cell transplantation device 10 is placed with the substrate surface 21S of the substrate 20 facing a surface of a skin Sk of the target transplantation site in the living body. The tips of the projection 30 are oriented toward the surface of the skin Sk.

As shown in FIG. 9, when the substrate 20 is pressed against the skin Sk, the skin Sk is punctured by the projection 30. That is, the penetrating portion is advanced into the skin Sk. Further, the cell transplantation device 10 may also include a mechanism for assisting the substrate 20 being pressed against the skin Sk. As the penetrating portion is advanced, the opening 32 is placed in the target region. When the cell group Cg is a hair follicle primordium, the target region is mainly an intradermal region.

As shown in FIG. 10, as the cell group Cg accommodated in the projection 30 exits via the opening 32, the cell group Cg is placed in the target region. FIG. 10 illustrates an example in which the cell transplantation device 10 includes a pressurizing unit 41 as a placement assisting portion that assists placement of the cell group Cg in the target region. As the pressurizing unit 41 applies a pressure, the cell group Cg and the storage liquid Lh are urged from the projection 30 to be placed in the target region.

In addition, even when the substrate 20 functions as the accommodating portion, the cell group Cg can be placed in the target region by allowing the cell group Cg to flow from the substrate 20, which is the accommodating portion, into the projection 30 and then releasing the cell group Cg from the opening 32 as long as the opening 32 of the projection 30 communicates with the accommodating portion.

As described above, since the cell transplantation device 10 includes the accommodating portion and the penetrating portion, penetration of the penetrating portion into the target region and release of the cell group Cg accommodated in the accommodating portion through the opening 32 placed in the target region by penetration of the penetrating portion can be continuously performed by a single device. Accordingly, compared with a transplantation method in which an incision is made in a transplantation site in the skin with a scalpel, and then cell groups are picked one by one with tweezers or the like and transferred from a culture container to the target site, the cells can be smoothly transplanted since the number of steps of exchanging the tools used can be reduced. Further, in a configuration in which the cell transplantation device 10 includes a plurality of projections 30, the cells can be further smoothly transplanted since the repeated operations of cutting the skin and repeated operations of flowing the cell group can be reduced.

As described above, in the form in which the projection 30 functions as the accommodating portion, it is preferred that the cell transplantation device 10 includes a plurality of accommodating portions and the cell groups Cg are accommodated in the respective accommodating portions. With this configuration, the cell transplantation device 10 can place the cell groups Cg accommodated in the respective accommodating portions into the skin Sk by a single release operation of the cell transplantation device 10.

Further, when the cell group Cg is released from the opening 32, the projection 30 is not always inserted into the skin Sk to the proximal end, that is, the substrate surface 21S is not always in contact with the surface of the skin Sk. For example, after the projection 30 is inserted into the skin Sk to the proximal end, the projection 30 may be pulled back to the extent that the opening 32 remains in the target region, and then the cell group Cg may be released at this position. With this configuration, since the cell group Cg is released at a position slightly above the bottom of the puncture made by penetration of the projection 30, a pressure that the released cell group Cg receives from the skin can be reduced compared with a case in which the cell group Cg is released on the bottom of the puncture. Accordingly, the cell groups Cg can be protected. In other words, the cell group Cg may be released while the projection 30 penetrates the skin Sk with the opening 32 being located inside the skin Sk, and the opening 32 may only be required to be placed in the target region at the timing of release.

With reference to FIGS. 11 to 18, a specific example, in which the cell group Cg is released after the projection 30 is pulled back inside the skin Sk, will be described.

Figure 11:
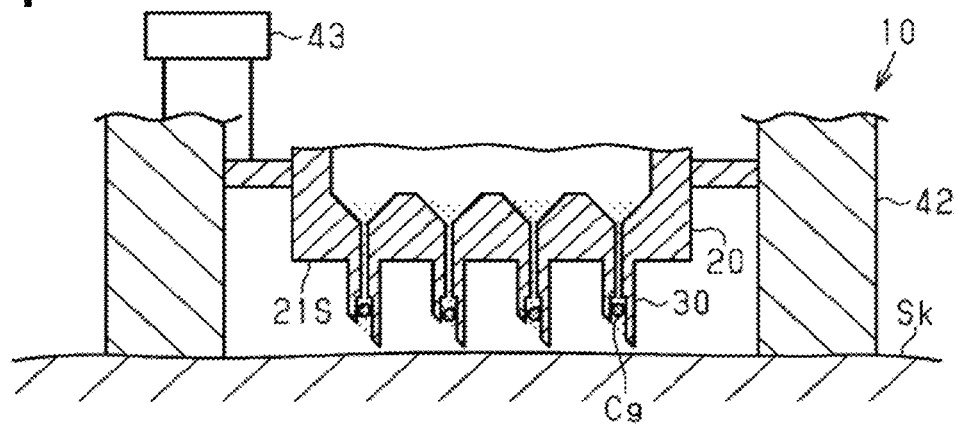
FIG. 11 is a view illustrating another example of a penetration step and a placement step of cell groups by using a cell transplantation device of an embodiment.

As shown in FIG. 11, the cell transplantation device 10 includes a penetration assistance member 42 outside the substrate 20. The penetration assistance member 42 is configured to be capable of abutting the skin Sk outside the substrate 20. The penetration assistance member 42 is provided continuously or intermittently along the outer periphery of the substrate 20.

The penetration assistance member 42 has a function of assisting control of the tension of the skin Sk when the projection 30 punctures the skin Sk. Further, the penetration assistance member 42 may also have a function of assisting alignment between the projection 30 and the surface of the skin Sk when the projection 30 punctures the skin Sk. Further, the penetration assistance member 42 may also have a function of assisting control of a penetrating direction of the projection 30 when the projection 30 punctures the skin Sk in a specific direction.

Moreover, the cell transplantation device 10 includes a positional adjustment unit 43 configured to be capable of changing the position of the substrate 20 and the projection 30 relative to the penetration assistance member 42 in the first direction. The positional adjustment unit 43 is connected to the penetration assistance member 42 and the substrate 20 and configured to be capable of changing the position of the penetration assistance member 42 relative to the substrate 20 and the projection 30 in the first direction by operation by the user of the cell transplantation device 10.

Figure 12:
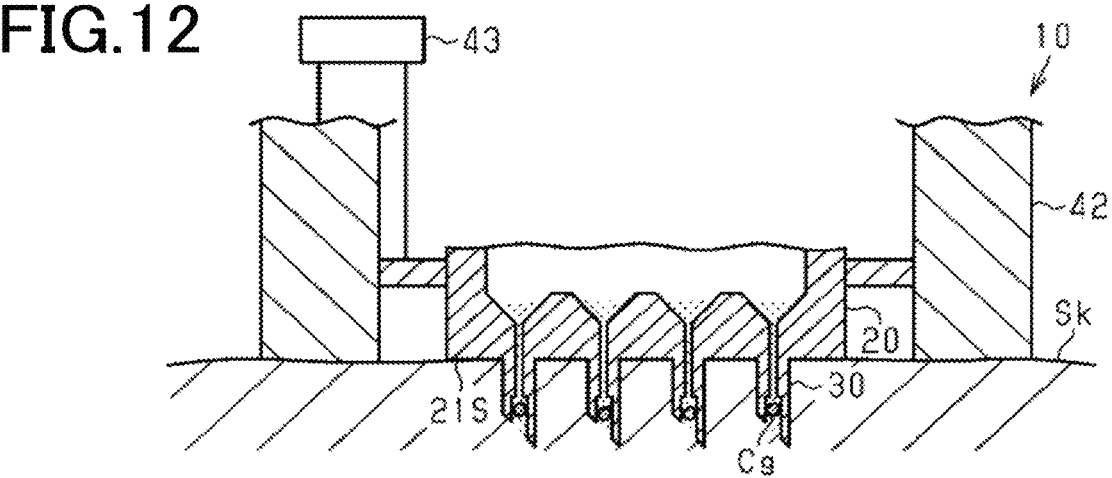
FIG. 12 is a view illustrating another example of a penetration step and a placement step of cell groups by using a cell transplantation device of an embodiment.

In the penetration step, the penetration assistance member 42 first abuts a portion of the surface of the skin Sk including the target transplantation site. Subsequently, as shown in FIG. 12, the substrate 20 and the projection 30 are moved relative to the penetration assistance member 42 until the protruding portion 30 protrudes from the penetration assistance member 42 and thus the projection 30 punctures the skin Sk. Here, the projection 30 deeply penetrates the skin Sk to the extent, for example, that the substrate surface 21S abuts the skin Sk. Since the skin Sk is held by the penetration assistance member 42, the position of the projection 30 relative to the skin Sk is stabilized, and thus the projection 30 can be smoothly advanced.

Figure 13:
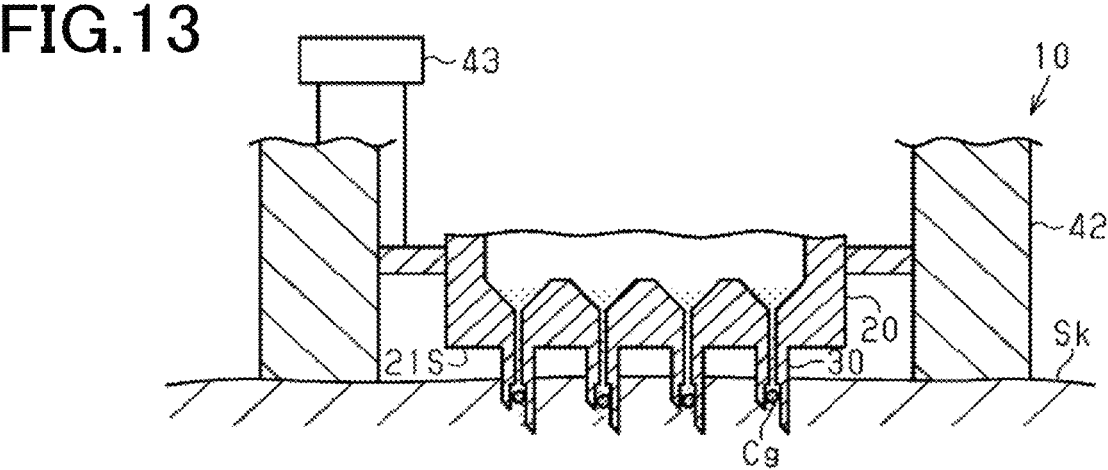
FIG. 13 is a view illustrating another example of a penetration step and a placement step of cell groups by using a cell transplantation device of an embodiment.

Subsequently, as shown in FIG. 13, the substrate 20 and the projection 30 are pulled back relative to the penetration assistance member 42, and the depth of advancement of the projection 30 is decreased. In this position, the cell group Cg is released from the projection 30 as the placement step.

Figure 14:
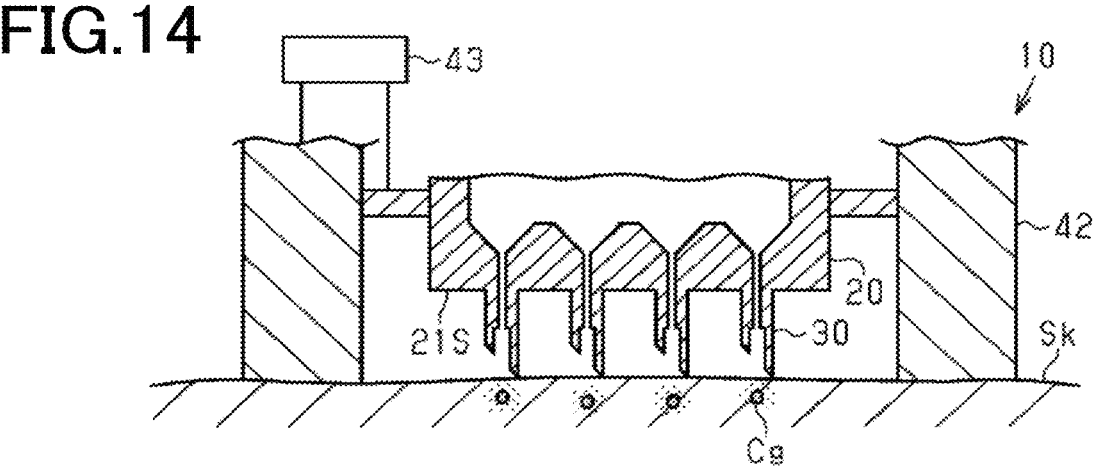
FIG. 14 is a view illustrating another example of a penetration step and a placement step of cell groups by using a cell transplantation device of an embodiment.

When release of the cell group Cg is completed, as shown in FIG. 14, the substrate 20 and the projection 30 are further pulled back relative to the penetration assistance member 42, and thus the projection 30 is removed from the skin Sk. Thus, transplantation of the cell group Cg is completed.

Figure 15:
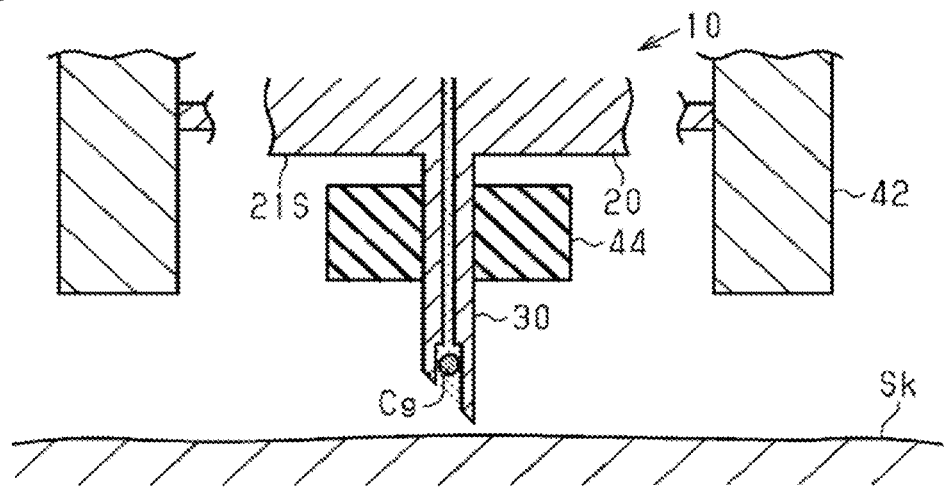
FIG. 15 is a view illustrating another example of a penetration step and a placement step of cell groups by using a cell transplantation device of an embodiment.

Further, the cell transplantation device 10 may also include an elastic body, and the projection 30 can be pulled back by using an elastic force of the elastic body. For example, as shown in FIG. 15, the cell transplantation device 10 includes an elastic body 44 that surrounds the projection 30. The elastic body 44 may be in contact with the substrate surface 21S, or may be separated from the substrate surface 21S. For example, the elastic body 44 is made of rubber, plastic, or the like.

Figure 16:
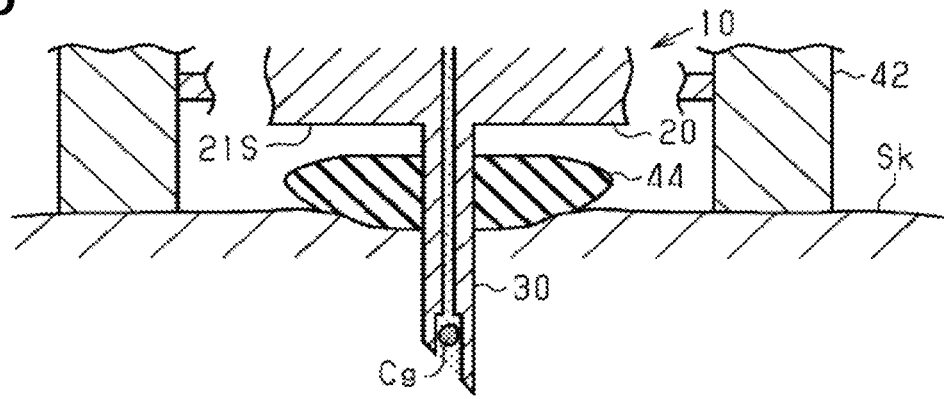
FIG. 16 is a view illustrating another example of a penetration step and a placement step of cell groups by using a cell transplantation device of an embodiment.

In the penetration step, the projection 30 and the elastic body 44 are first pressed against the surface of the skin Sk of the target transplantation site. Accordingly, as shown in FIG. 16, the elastic body 44 deforms and collapses, and a portion of the projection 30 protruding from the elastic body 44 punctures the skin Sk. Further, the cell transplantation device 10 may include the penetration assistance member 42 so as to assist the projection 30 to be advanced.

Figure 17:
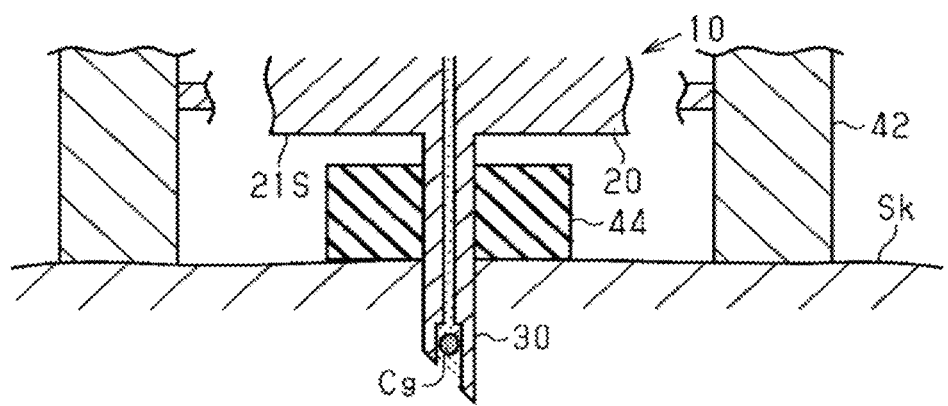
FIG. 17 is a view illustrating another example of a penetration step and a placement step of cell groups by using a cell transplantation device of an embodiment.

Subsequently, as shown in FIG. 17, as the force pressing the elastic body 44 is reduced, the elastic body 44 deforms and returns to the initial shape. That is, the collapse of the elastic body 44 is mitigated. The projection 30 is pulled back while the elastic body 44 deforms, and the depth of advance of the projection 30 is decreased. In this position, the cell group Cg is released from the projection 30 as the placement step. Further, at the time of release of the cell group Cg, the elastic body 44 may not necessarily completely return to the initial shape. In addition, the projection 30 can also be pulled back by using both the positional adjustment of the projection 30 by using the positional adjustment unit 43 and the elastic force of the elastic body 44.

Figure 18:
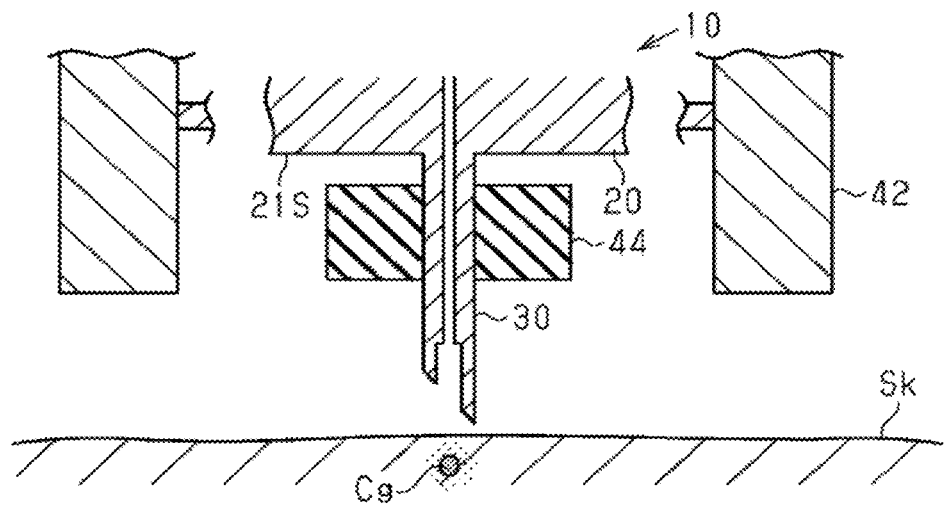
FIG. 18 is a view illustrating another example of a penetration step and a placement step of cell groups by using a cell transplantation device of an embodiment.

When release of the cell group Cg is completed, as shown in FIG. 18, the elastic body 44 and the projection 30 are pulled back, and thus the projection 30 is removed from the skin Sk. Thus, transplantation of the cell group Cg is completed.

Further, the elastic body 44 may be disposed at a position outside the substrate 20 and surrounding the entirety of the plurality of projections 30.

In the penetration step, the projection 30 may puncture the skin Sk in a direction perpendicular to the surface of the skin Sk, or may puncture the skin Sk in a direction inclined relative to the surface of the skin Sk.

Figure 19:
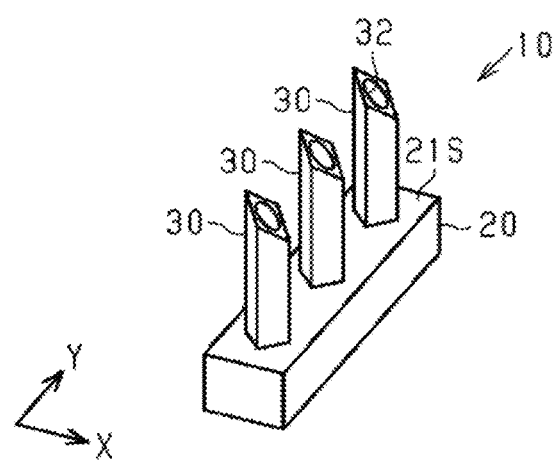
FIG. 19 is a view illustrating a perspective structure of an example of arrangement of projections in a cell transplantation device of an embodiment.

With reference to FIG. 19, an example of the cell transplantation device 10 suitable for puncturing the skin Sk by the projection 30 in a direction inclined relative to the surface of the skin Sk will be described.

Figure 20:
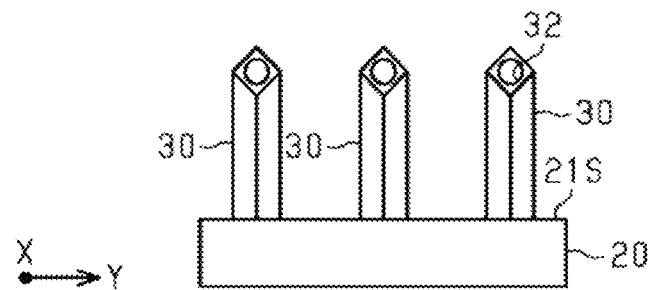
FIG. 20 is a view illustrating a front structure of an example of arrangement of projections in a cell transplantation device of an embodiment.
Figure 21:
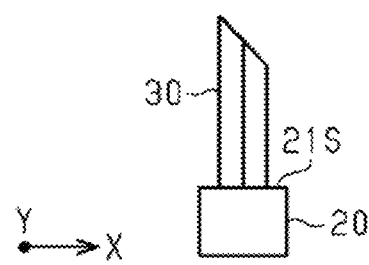
FIG. 21 is a view illustrating a side structure of an example of arrangement of projections in a cell transplantation device of an embodiment.

As shown in FIG. 19, a plurality of projections 30 are arranged in a line in the Y direction, which is a second direction, on the substrate surface 21S of the substrate 20. When viewing along this second direction, one array of the projections 30 is arranged in the X direction, which is perpendicular to the Y direction. That is, only one line made up of the plurality of projections 30 is disposed on the substrate surface 21S. As shown in FIG. 20, when viewed in the direction parallel to the X direction, all the plurality of projections 30 are visually observed, and these projections 30 are arranged in line. As shown in FIG. 21, when viewed in the direction parallel to the Y direction, the plurality of projections 30 are overlapped with each other.

The plurality of projections 30 are preferably arranged oriented in the same direction in a plane extending in the Y direction, that is, in the second direction. In other words, the plurality of projections 30 are preferably arranged with the openings 32 being oriented in one direction. Here, the tips of the plurality of projections 30 are also oriented in one direction. The tips of the plurality of projections 30 are preferably located on the edge of the respective projections 30 in the X direction.

Figure 22:
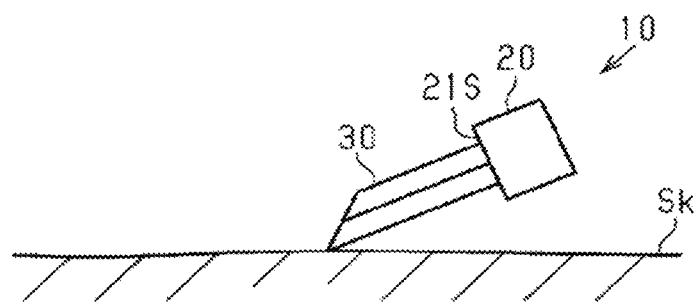
FIG. 22 is a view illustrating an example of placement of a cell transplantation device when a penetration step of cell groups is performed by using a cell transplantation device of an embodiment.
Figure 23:
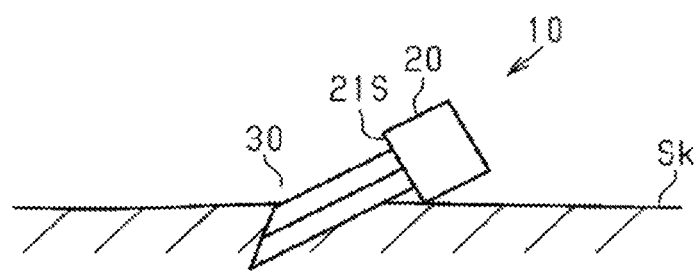
FIG. 23 is a view illustrating an example of a penetration step of cell groups by using a cell transplantation device of an embodiment.

According to the configuration in which the plurality of projections 30 are arranged in a line, the respective projections 30 can puncture the skin to a uniform depth even if the cell transplantation device 10 is disposed on the surface of the skin Sk with an angle. That is, as shown in FIG. 22, the cell transplantation device 10 is disposed such that the projection 30 extends in a direction inclined relative to the surface of the skin Sk. Here, the cell transplantation device 10 is disposed with the Y direction extending along the surface of the skin Sk. The substrate surface 21S is inclined relative to the surface of the skin Sk. As shown in FIG. 23, when the projection 30 is advanced into the skin Sk in the extending direction of the projection 30, the projection 30 can puncture the skin Sk in the above inclined direction. Since the projection 30 is inclined relative to the surface of the skin Sk, an angle of the projection 30 relative to the skin Sk can be easily adjusted to an angle that facilitates puncture of the skin Sk by the projection 30. Further, the opening 32 can be easily disposed at a shallow position in the skin Sk.

In particular, a configuration in which the plurality of projections 30 are oriented in the same direction facilitates uniform puncture of the skin Sk by the respective projections 30. Further, a configuration in which the distal ends of the plurality of projections 30 are located on the edge of the respective projections 30 in the X direction facilitates puncture of the skin Sk by the projections 30 since the tips of the respective projections 30 are aligned with each other when puncturing the skin Sk. Further, even when the plurality of projections 30 are arranged in a line, the cell transplantation device 10 may also be used so that the projections 30 vertically puncture the skin in a direction facing the surface of the skin Sk.

In other configurations, the distal region of the projection 30 may also be formed to be widened in the skin Sk regardless of the direction of puncture by the projections 30. When the distal region of the projection 30 is formed to be widened in the skin Sk, the distal region of the projection 30 spreads out the tissues of the skin to thereby expand the hole created by the projection 30. Accordingly, since a large space into which the cell group Cg is placed can be ensured, a pressure that the released cell group Cg receives from the skin can be reduced. Thus, the cell groups Cg can be protected.

Further, when the cell transplantation device 10 includes the plurality of projections 30, the positions where the openings 32 are placed in the depth direction in the skin Sk may not be necessarily constant in the plurality of projections 30. For example, when the lengths of the projections 30 or the positions of the openings 32 of the projections 30 are different from each other in the plurality of projections 30, the cell transplantation device 10 having the projections 30 whose openings 32 are placed in the intradermal layer and the projections 30 whose openings 32 are placed in the subcutaneous layer can be achieved.

When the substrate 20 is pressed against the skin Sk until the substrate surface 21S is placed on the surface of the skin Sk, the projections 30 can be easily inserted into the skin Sk to the proximal end, and the lengths of the projections 30 inserted into the skin Sk can be prevented from varying depending on the positions of the projections 30 on the substrate surface 21S. From this point of view, it is preferred that the substrate 20 has flexibility and is deformable along the surface of the skin Sk, since the substrate surface 21S can easily extend along the surface of the skin Sk. Further, when the substrate surface 21S is a curved surface, the substrate surface 21S can also easily extend along the surface of the skin Sk. In this case, for example, the substrate surface 21S is formed as a curved surface having a curvature similar to the curvature of the surface of the skin Sk at the transplantation site. The shape of the substrate surface 21S is not specifically limited, and the substrate surface 21S may be a circular shape, a polygonal shape, or other shapes.

<Placement Assisting Portion>

A configuration of the placement assisting portion that assists placement of the cell group Cg into the target region will now be described. The placement assisting portion may have a function of assisting release of the cell groups Cg from the cell transplantation device 10, a function of assisting placement of the cell groups Cg in the direction extending along the skin surface, or a function of assisting placement of the cell groups Cg in the depth direction of the skin. Further, the placement assisting portion may also have a plurality of functions among these functions.

First, a configuration of the pressurizing unit 41 shown in FIG. 10 will be described as the placement assisting portion having a function of assisting release of the cell groups Cg. The pressurizing unit 41 applies pressure to the liquid material containing the cell group Cg and the storage liquid Lh by supplying gas or liquid into an internal space of the substrate 20 and an internal space of the projection 30 to thereby push out the cell group Cg together with the storage liquid Lh to the outside via the opening 32. The pressurizing unit 41 has a mechanism of releasing gas or liquid, or a pressurizing structure including a piston or the like.

The gas used for pressurization is air, for example. When gas is used for pressurization, the pressurizing unit 41 feeds the gas from the internal space of the substrate 20 into the opening 32 of the projection 30. When pushed by air, the cell group Cg and the storage liquid Lh accommodated in the projection 30 exit through the opening 32.

When liquid is used for pressurization, the pressurizing unit 41 feeds the liquid from the internal space of the substrate 20 into the opening 32 of the projection 30. When pushed by the liquid, the cell group Cg and the storage liquid Lh accommodated in the projection 30 exit through the opening 32. The liquid used for pressurization is physiological saline, for example. As described above in connection with the step of accommodating the cell group Cg, when the storage medium Lh is replaced by physiological saline, introduction of a liquid for release of the cell group Cg can be continuously performed after the replacement of the storage liquid Lh.

Alternatively, the pressurizing unit 41 may apply pressure to the liquid material accommodated in the projection 30 by using a structure such as a piston without supplying new liquid.

Figure 24:
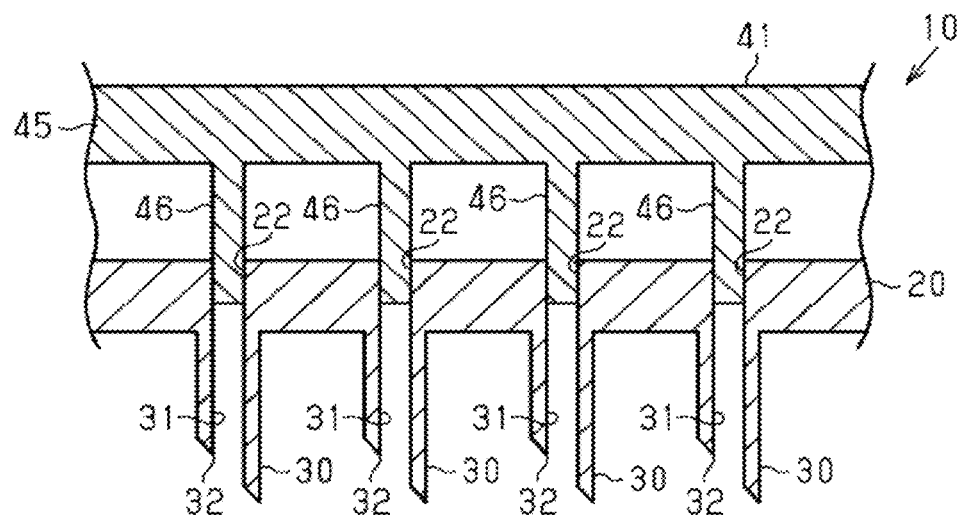
FIG. 24 is a view illustrating a cell transplantation device that includes a piston-like structure in a cell transplantation device of an embodiment.

FIG. 24 illustrates a form in which the cell transplantation device 10 having a plurality of projections 30 includes a piston-like structure as an example of the pressurizing unit 41. The pressurizing unit 41 includes a plate-shaped support portion 45 and a plurality of insertion portions 46 protruding from the support portion 45. The insertion portion 46 has an outer diameter that can be inserted into the internal channel 31 of the projection 30. The plurality of insertion portions 46 are disposed on the support portion 45 corresponding to the arrangement of the internal channels 31 of the plurality of projections 30. That is, the plurality of insertion portions 46 are disposed such that each insertion portion 46 is assigned to a respective internal channel 31.

Figure 25:
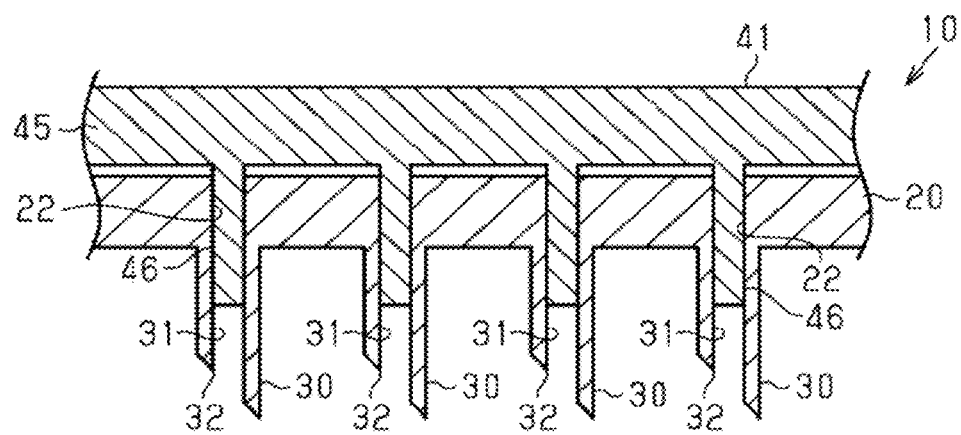
FIG. 25 is a view illustrating a cell transplantation device that includes a piston-like structure in a cell transplantation device of an embodiment.

In the placement step, the insertion portions 46 are inserted into the internal channels 31 of the respective projections 30 from the end that does not have the opening 32. Specifically, the insertion portions 46 enter the internal channels 31 through the proximal flow paths 22 in the substrate 20 as shown in FIG. 25. As the insertion portions 46 are inserted, gas or liquid in the internal channels 31 are pressed. Accordingly, the cell group Cg and the storage liquid Lh accommodated in the projection 30 exit the openings 32.

Further, the piston-like structure composed of the support portion 45 and the insertion portion 46 can also be used as a member for drawing the liquid material containing the cell group Cg into the internal channel 31 in the accommodating step. That is, as the support portion 45 and the insertion portion 46 are pulled up to remove the insertion portion 46 from the internal channel 31, the liquid material containing the cell group Cg is drawn into the internal channel 31 via the opening 32. The piston-like structure composed of the support portion 45 and the insertion portion 46 may be used only in the accommodating step or in the placement step, or may be used in both the accommodating step and the placement step.

FIGS. 24 and 25 illustrate a form in which the internal channel 31 of the projection 30 has the constant internal diameter. When the accommodating step and the placement step are performed by using the piston-like structure composed of the support portion 45 and the insertion portion 46, for example, the cell group Cg drawn into the internal channel 31 can be retained in the internal channel 31 by holding the distal end of the insertion portion 46, which has been pulled back in the accommodating step, near the boundary between the internal channel 31 and the proximal flow path 22 of the substrate 20. Further, FIGS. 24 and 25 illustrates an example in which the substrate 20 does not include the intermediate flow path 23. However, the substrate 20 may include the intermediate flow path 23, and the support portion 45 and the proximal portion of the insertion portion 46 may have a shape corresponding to the shape of the flow path in the substrate 20.

Furthermore, the placement assisting portion may assist release of the cell groups Cg by the action of a chemical. For example, the inner wall of the internal channel 31 near the opening 32 may be provided with hydrophobicity to promote release of the liquid material containing the cell group Cg via the opening 32. In this case, a portion to which hydrophobicity is imparted functions as the placement assisting portion.

In addition, the placement assisting portion may also include a mechanism capable of controlling the timing when the cell group Cg is released via the opening 32. With this configuration, the cell group Cg can be released at a desired timing while the projection 30 is pulled back from the skin, for example, after the projection 30 punctures the skin. Accordingly, the positions where the cell groups Cg are placed in the depth direction of the skin can be controlled. Such a placement assisting portion also functions as a placement assisting portion that assists placement of the cell groups Cg in the depth direction of the skin.

Further, in a configuration in which the plurality of cell groups are accommodated in the accommodating portion, the placement assisting portion may include a mechanism for releasing the cell groups Cg one by one via the opening 32 by changing the pressure applied to the liquid material in the accommodating portion. The cell group Cg may also flow out from the opening 32 due to a pressure difference between the target region and the inside of the projection 30 without being assisted by the placement assisting portion. However, the configuration in which release of the cell group Cg is assisted by the placement assisting portion is preferred in that the release of the cell group Cg is smoothly performed.

The placement assisting portion having a function of assisting placement of the cell groups Cg in a direction parallel to the surface of the skin may be, for example, a placement assisting portion having a camera for imaging the skin surface. Since a region of the skin surface to be punctured by the projection 30 can be determined on the basis of the image captured by the camera, a transplantation position can be set precisely. Further, when the puncture depth of the projection 30 can be determined by using analysis of an image captured by the camera, the placement assisting portion also functions as a placement assisting portion that assists placement of the cell group Cg in the depth direction of the skin.

Further, when the placement assisting portion has a camera, the camera can also be used in the accommodating step of accommodating the cell group Cg into the accommodating portion. That is, the positions of the cell groups Cg in the tray 50 and the positions of the projections 30 can be aligned with each other by using an image captured by the camera. Since the positions can be aligned in accommodation of the cell groups Cg by using a camera, the projections 30 can be prevented from deforming due to contact between the projection 30 and the tray 50 in accommodation of the cell groups Cg.

Further, the placement assisting portion may also include a function of facilitating puncture of the skin by the projection 30 as a function of assisting placement of the cell groups Cg in the depth direction of the skin. For example, the placement assisting portion may also include a mechanism for adjusting the temperature of at least one of the substrate surface 21S, the projection 30, and the skin surface. Specifically, the placement assisting portion includes a heating mechanism or a cooling mechanism. The temperature of the skin can be adjusted directly or via the substrate surface 21S or the projection 30 to thereby adjust the tension and elasticity of the skin. Accordingly, the skin condition can be controlled to be suitable for puncture by the projection 30.

<Configuration Suitable for Transplantation of Hair Follicle Primordium>

Figure 26:
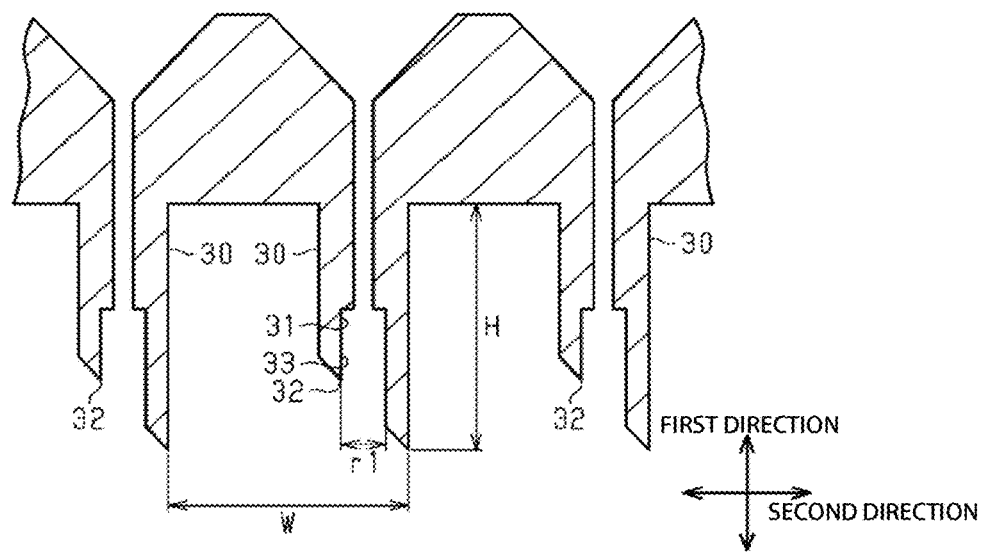
FIG. 26 is an enlarged view illustrating a cross-sectional structure of a cell transplantation device of an embodiment.

When the cell group Cg is a hair follicle primordium, placing the cell group Cg at an appropriate position in each of the depth direction of the skin and the direction extending along the skin surface contributes to good hair growth from the hair follicle, which is formed from the hair follicle primordium. With reference to FIG. 26, a configuration suitable for transplantation of hair follicle primordia including a configuration for placement of the cell groups Cg will be described. In addition, when hair follicle primordia are transplanted, a human scalp is mainly assumed as a site of transplantation.

As described above, the hair follicle primordium is formed, for example, by culturing a mixture of mesenchymal cells derived from mesenchymal tissues such as dermal papilla and epithelial cells derived from epithelial tissues located in a bulge region or a hair bulb base under predetermined conditions. When the cell group Cg is a hair follicle primordium, a liquid material containing the hair follicle primordium, and a storage liquid, which is a liquid for protecting the hair follicle primordium, may further include other components.

As shown in FIG. 26, an opening area of the opening 32 on the peripheral surface of the projection 30 is preferably in the range of 5000 $\mu m^2$ or more and 300000 $\mu m^2$ or less. The shape of the opening 32 is not specifically limited, and may be, for example, a circular shape or an elliptical shape. An internal diameter of the internal channel 31 in a portion having the opening 32, that is, the first internal diameter r1 of the large diameter portion 33 is preferably in the range of 100 $\mu m$ or more and 600 $\mu m$ or less when the large diameter portion 33 is a cylindrical hole. Since the opening 32 does not become too small for the hair follicle primordium as long as the opening area and the internal diameter r1 are equal to or larger than the above lower limit, an opening 32 having a sufficient size for the hair follicle primordia smoothly flowing in and out of the opening 32 can be achieved. In addition, since the opening 32 does not become too large relative to the hair follicle primordium as long as the opening area and the internal diameter r1 are equal to or smaller than the above upper limit, an opening 32 that allows the hair follicle primordia to flow in and out one by one can be achieved.

The length H of the projection 30 is a length in the first direction from the proximal end to the distal end of the projection 30. The length H of the projection 30 is preferably in the range of 200 $\mu m$ or more and 6 mm or less. When the length H of the projection is within the above range, the projection 30 suitable for placement of the opening 32 in the target region can be achieved. In a configuration in which the cell transplantation device 10 includes a plurality of projections 30, the length H of the plurality of projections 30 may not necessarily be the same.

The cell transplantation device 10 may include a plurality of projections 30 or a single projection 30. For example, the cell transplantation device 10 having the plurality of projections 30 is used for a large transplantation site, and the cell transplantation device 10 having a single projection 30 is used for a small transplantation site or an end region of a transplantation site.

When the cell transplantation device 10 has a plurality of projections 30, the positions of the hair follicle primordia in a direction parallel to the skin surface is determined according to the positions of the plurality of projections 30 on the substrate surface 21S. That is, the positions where hair grows in the transplantation site are generally determined according to the positions of the plurality of projections 30 on the substrate surface 21S.

The plurality of projections 30 may be regularly or irregularly positioned on the substrate surface 21S, and the positioning of the projections 30 may be set depending on desired positions of the hair follicle primordia. When the projections 30 are regularly positioned, the projections 30 are positioned, for example, in a square lattice structure or a hexagonal lattice structure on the substrate surface 21S. Further, as described above, the projections 30 may also be arranged in a line. Alternatively, positioning of the projections 30 may also be set according to the arrangement of the pores of the object that receives transplantation in the vicinity of the transplantation site.

The density of the projections 30 per unit area on the substrate surface 21S is preferably $1/cm^2$ or more and $400/cm^2$ or less, and more preferably $20/cm^2$ or more and $100/cm^2$ or less. When the density of the projections 30 is equal to or larger than the above lower limit, the density of hair that grow from the hair follicle primordia will be sufficient for hair density. When the density of the projections 30 is equal to or smaller than the above upper limit, nutrients are easily distributed to the hair follicle primordia that are positioned in the skin at the same density as that of the projection 30. Accordingly, formation of hair follicles and hair proceeds advantageously.

An interval W, which is a distance between the adjacent projections 30, is preferably in the range of 1 mm or more and 4 mm or less. The interval W is a distance in the second direction between the ends of the adjacent projections 30 that face the same orientation. When the interval W is equal to or larger than the above lower limit, the processing accuracy for the projection 30 can be easily obtained. When the interval W is equal to or smaller than the above upper limit, the density of hair that grows from the hair follicle primordia will be sufficient for hair density.

An area of the substrate surface 21S including a portion in which the projections 30 are disposed is preferably in the range of $0.005\ cm^2$ or more and $4\ cm^2$ or less. When the area of the substrate surface 21S is equal to or larger than the above lower limit, the processing accuracy for the substrate 20 can be easily obtained. When the area of the substrate surface 21S is equal to or smaller than the above upper limit, the substrate surface 21S easily follows the scalp when the substrate 20 is pressed against the scalp, since the extending area of the substrate surface 21S, even if it is a flat surface, is not too large to follow a curvature of the scalp.

In addition, the entirety of the projection 30 may function as the penetrating portion, or part of the projection 30 may function as the penetrating portion. In either case, a length corresponding to the above length H is the length of a portion of the projection 30 which functions as the penetrating portion, that is, the length of a portion inserted into the skin is preferably in the range of 200 $\mu m$ or more and 6 mm or less.

Figure 27:
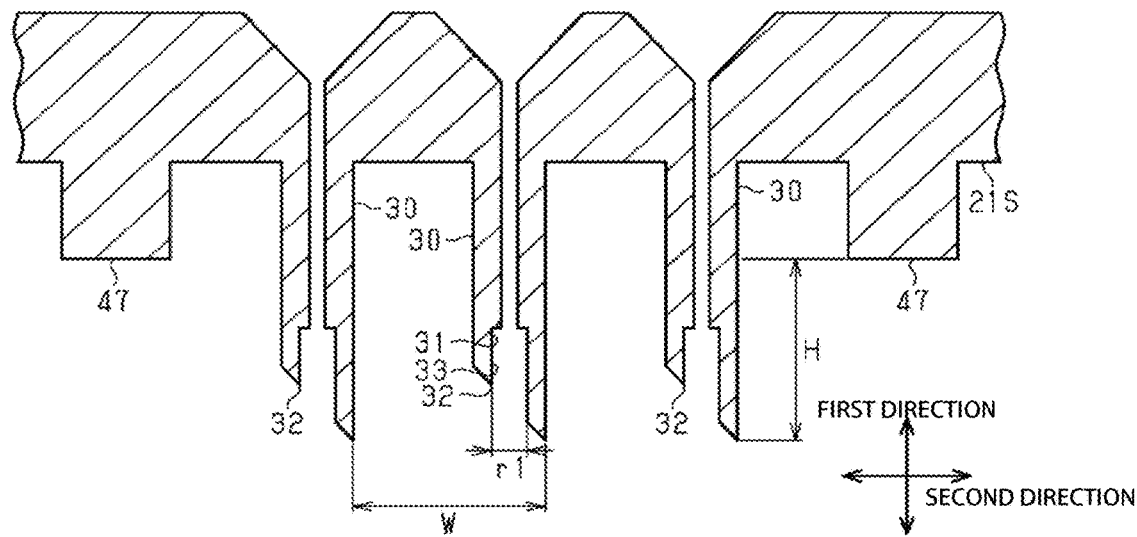
FIG. 27 is a view illustrating another example of a cross-sectional structure of a cell transplantation device of an embodiment.

For example, as shown in FIG. 27, the cell transplantation device 10 includes a penetration control unit 47 protruding from the substrate surface 21S. The penetration control unit 47 is disposed outside a region in which the projection 30 is disposed when viewed in the first direction. In this configuration, the penetration control unit 47 abuts the skin surface when the projection 30 punctures the skin. Accordingly, a portion of the projection 30 protruding from the penetration control unit 47 in the first direction punctures the skin. In this case, a length of the portion protruding from the penetration control unit 47 in the first direction is the length H that functions as the penetrating portion of the projection 30.

Figure 28:
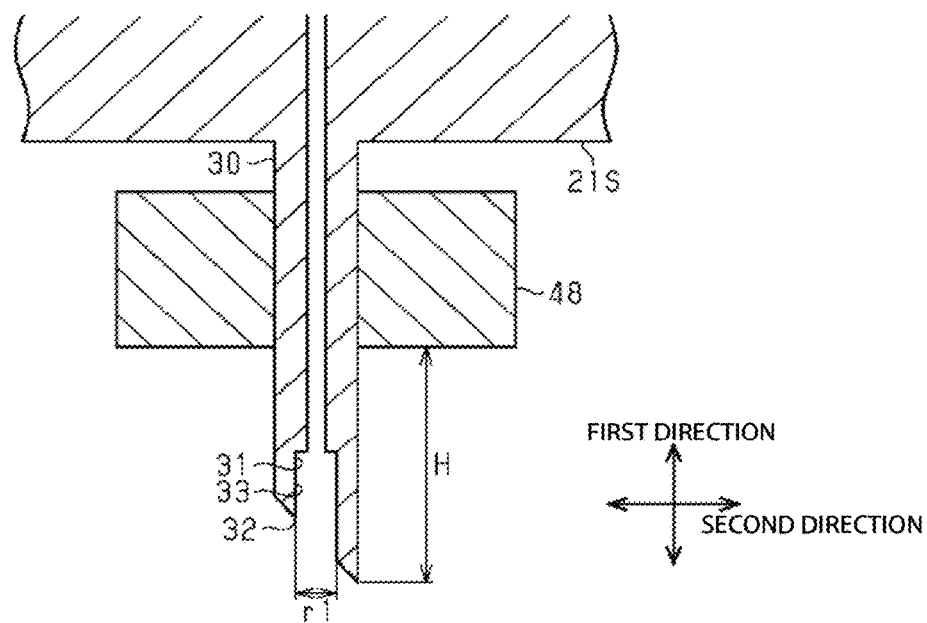
FIG. 28 is a view illustrating another example of a cross-sectional structure of a cell transplantation device of an embodiment.

For example, as shown in FIG. 28, the cell transplantation device 10 may further include a penetration control unit 48 that surrounds the projection 30. The penetration control unit 48 may be in contact with the substrate surface 21S, or may be separated from the substrate surface 21S. In the configuration having the penetration control unit 48, the penetration control unit 48 abuts the skin surface when the projection 30 punctures the skin. Accordingly, a portion of the projection 30 protruding from the penetration control unit 48 in the first direction punctures the skin. In this case, a length of the portion protruding from the penetration control unit 48 in the first direction is the length H that functions as the penetrating portion of the projection 30. In the above examples, the penetration control units 47 and 48 have a rigidity equal to or larger than that of the projection 30.

When the cell group Cg is a hair follicle primordium, in the form in which the projection 30 functions as the accommodating portion, it is preferred that the cell transplantation device 10 includes a plurality of accommodating portions and the hair follicle primordia are accommodated in the respective accommodating portions. The cell transplantation device 10 is preferably configured to take the hair follicle primordia placed in the tray 50 into each of the plurality of accommodating portions by one operation. Further, the cell transplantation device 10 is preferably configured to place the hair follicle primordia accommodated in the respective accommodating portions into the skin Sk by a single release operation of the cell transplantation device 10. Further, for the cell groups Cg, which are hair follicle primordia, it is preferred that each hair follicle primordium is separated from others when placed in the tray 50, and each hair follicle primordium is accommodated in the respective accommodating portions.

<Material and Production Method for Cell Transplantation Device>

Materials for forming the projection 30 are not specifically limited. For example, the projection 30 may be made of silicon, metal materials such as stainless steel, titanium, cobalt-chromium alloy, and magnesium alloy, or may be made of polymer materials such as commodity plastics, medical grade plastics, and plastics for cosmetic products. Examples of the polymer material include, polyethylene, polypropylene, polystyrene, polyamide, polycarbonate, cyclic polyolefin, polylactic acid, polyglycolic acid, polycaprolactone, acrylic, urethane resin, aromatic polyether ketone, epoxy resin, polysaccharide, polyarylate, polyetherimide, polyamino acid, and copolymer materials of these resins. Further, the projection 30 may be made of ionizing radiation curable materials such as polyacrylic, and thermosetting materials such as urethane and epoxy. Materials for forming the substrate 20 are also not specifically limited, and the substrate 20 may be made of, for example, materials described above as the materials for the projection 30. The projection 30 and the substrate 20 may be made of the same materials or different materials.

Preferably, the projection 30 and the substrate 20 are made of polymer materials. Producing the projection 30 and the substrate 20 by using polymer materials is advantageous in that it has a high degree of design freedom, is suitable for mass production, enables incineration after use, enables selection of a transparent material, and allows direct observation of accommodated objects including cell groups when a transparent material is selected.

The substrate 20 and the projection 30 may be integrally formed as a unitary molded product, or may be separately formed and then joined together. The substrate 20 and the projection 30 can be produced by using known machining methods, or resin molding methods such as injection molding.

Figure 29:
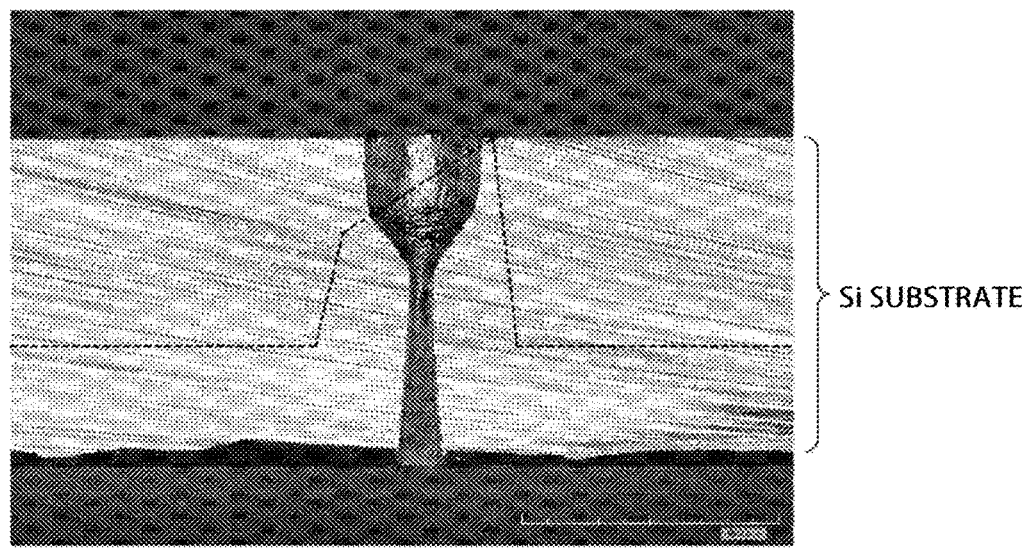
FIG. 29 is an image of a structure from which a substrate and a projection of a cell transplantation device of an embodiment is being formed.

FIG. 29 is an image of a structure from which the projection 30 and the substrate 20 are being formed. FIG. 29 illustrates a cross-section of a structure of a phase in which a hole to be provided as the internal channel 31 and the proximal flow path 22 is formed in a silicon substrate. The structure shown in FIG. 29 undergoes processing such as grinding to form an outer shape of the projection 30, as indicated by the dotted line of FIG. 29. Thus, the projection 30 and the substrate 20 are formed. Further, in the projection 30 formed from the structure shown in FIG. 29, the internal diameter of the internal channel 31 gradually changes from the large diameter portion 33 to the small diameter portion 34.

Figure 30:
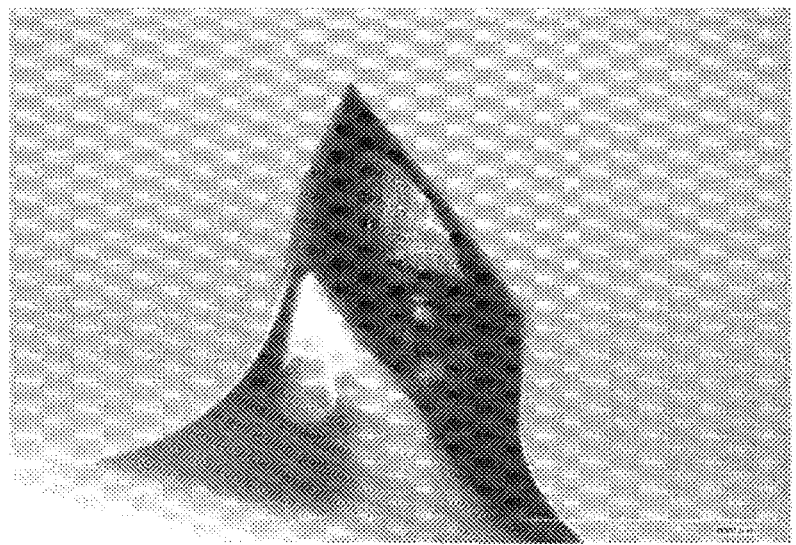
FIG. 30 is an image of a projection formed by processing the structure of FIG. 29.

FIG. 30 is an image of the projection 30 formed by grinding of the structure shown in FIG. 29. In the image of FIG. 30, since liquid droplets are attached near the proximal end of the projection 30, the outer shape near the proximal end appears as a curved shape.

<Cell Transplantation Unit>

With reference to FIGS. 31 to 40, the cell transplantation unit will now be described.

Figure 31:
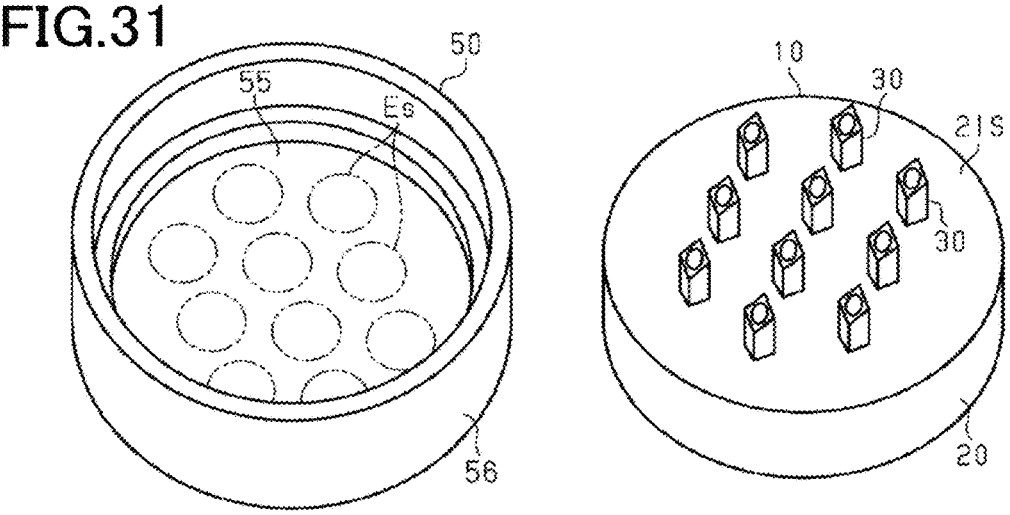
FIG. 31 is a view illustrating a perspective structure of a tray and a cell transplantation device which constitute a cell transplantation unit in an embodiment of a cell transplantation unit.

As shown in FIG. 31, the cell transplantation unit includes the cell transplantation device 10 and the tray 50 in which cell groups are placed. The tray 50 includes a flat bottom 55 and a side wall 56 extending from the outer periphery of the bottom 55. The bottom 55 has one or more placement region Es, which are regions where cell groups are to be placed, on a surface of the bottom 55. The placement region Es is embodied, for example, as a part having surface characteristics such as surface roughness and wettability different from those of the other regions, or as a part that can be distinguished from the other regions by difference in color or by providing a frame line.

In the placement region Es, the cell group and the protective liquid are held. For example, the tray 50 is a culture container, and a cell group is formed by culturing cells on the bottom 55. Alternatively, a cell group can also be formed by culturing cells in a culture container different from the tray 50, and then the cell group can be transferred on the bottom 55. When the protective liquid is a gel, the cell group can be separated for each cell group, together with the protective liquid, and placed on the bottom 55. The cell group can be accommodated in the cell transplantation device 10 from the tray 50, and the accommodated cell group is transferred to the target region in the living body to thereby achieve transplantation of cell groups. Materials for the tray 50 is not specifically limited, and the tray 50 can be made of a material meeting the culture conditions and the like by a production method suitable for the material.

Figure 32:
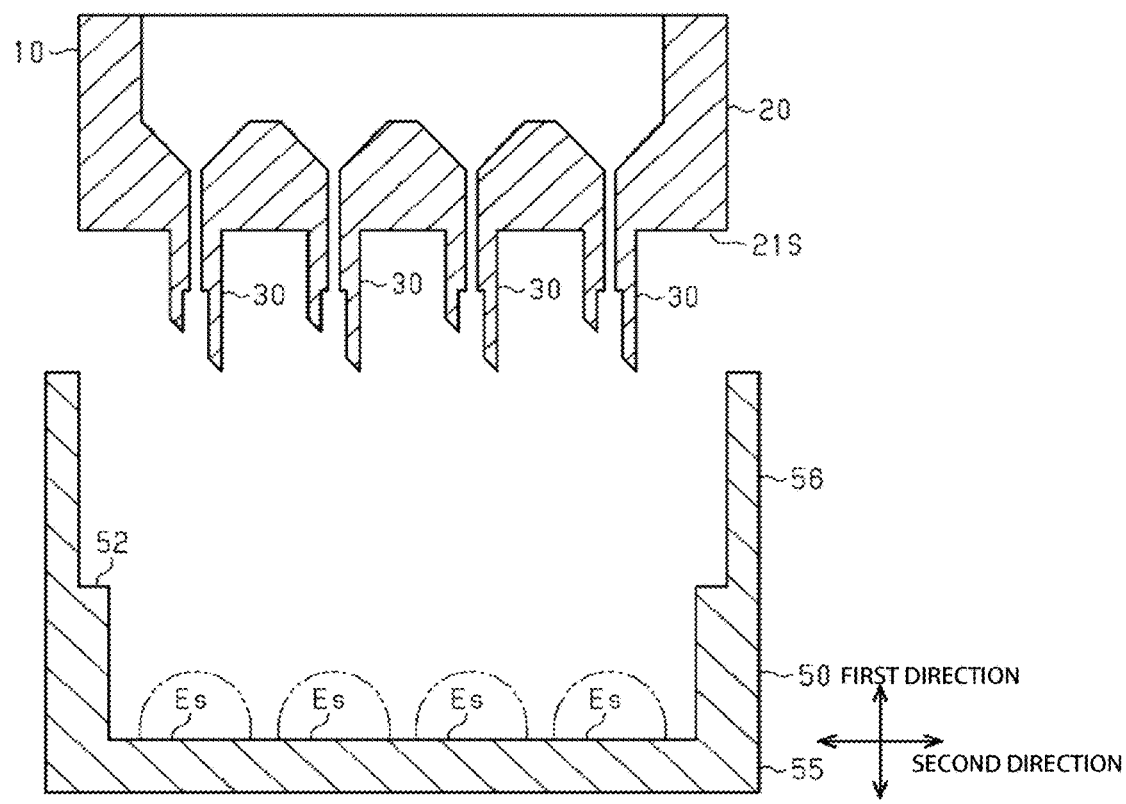
FIG. 32 is a view illustrating placement of a tray and a cell transplantation device when an accommodating step is performed in a cell transplantation unit of an embodiment.

As shown in FIG. 32, the amount and arrangement of the placement regions Es in the tray 50 and the amount and arrangement of the projections 30 in the cell transplantation device 10 are set such that each projection 30 corresponds to a respective placement region Es. That is, when the tray 50 and the cell transplantation device 10 face each other in the first direction, each projection 30 face a respective placement region Es. In other words, each projection 30 is assigned to a respective placement region Es such that the placement region Es and the projection 30 correspond to each other one to one. FIG. 32 illustrates a configuration in which the tray 50 has a plurality of placement regions Es and the cell transplantation device 10 has a plurality of projections 30. The configuration is merely an example, and when the tray 50 has one placement region Es and the cell transplantation device 10 has one projection 30, the placement region Es and the projection 30 correspond to each other one to one as long as the placement region Es and the projection 30 are disposed to face each other.

Since one projection 30 is assigned to one placement region Es, the amount of cell groups taken into one projection 30 can be adjusted by adjusting the amount of cell groups placed in one placement region Es. Accordingly, it is easy to accommodate a predetermined amount of cell groups in a plurality of projections 30.

Figure 33:
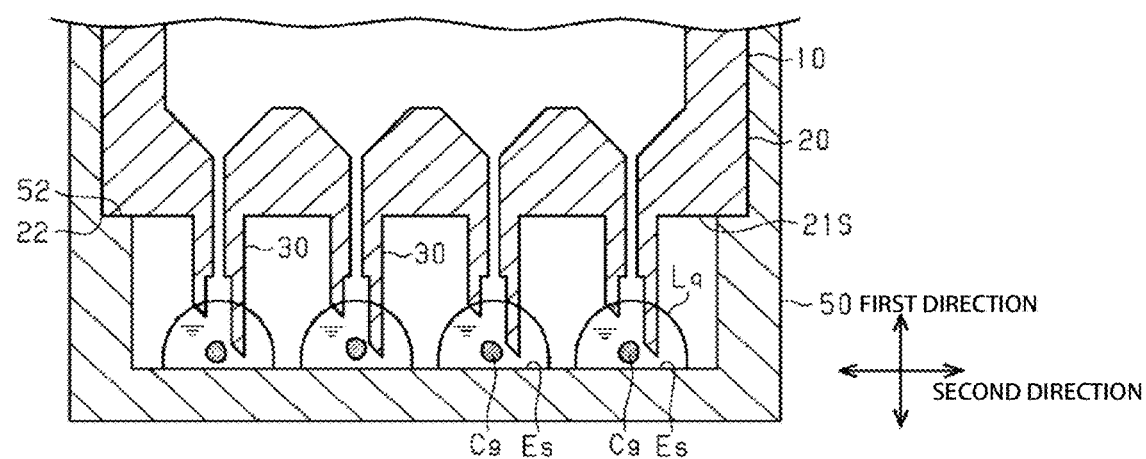
FIG. 33 is a view illustrating an accommodating step of cell groups by using a cell transplantation unit of an embodiment.

As shown in FIG. 33, one cell group Cg is held in each placement region Es of the tray 50. In accommodation of cell groups Cg into the cell transplantation device 10, as previously described in connection with the accommodating step, the distal region of one projection 30 is directed to one placement region Es, and the cell group Cg together with the protective liquid Lq is taken into the projection 30 via the opening 32.

Preferably, the tray 50 and the cell transplantation device 10 include a positioning structure that regulates a position of the projection 30 relative to a position of the placement region Es in the first direction, that is, in the depth direction of the tray 50. The positioning structure regulates the distance between the placement region Es and the distal region of the projection 30 to a length suitable for taking in the cell groups Cg.

Specifically, the positioning structure is composed of an end of the substrate surface 21S of the cell transplantation device 10, and a shoulder 52 provided along the inner surface of the side wall 56. The shoulder 52 protrudes from the side wall 56 to the inside of the tray 50, and an upper surface of the shoulder 52 abuts the end of the substrate surface 21S when the cell transplantation device 10 is inserted inside the tray 50. Accordingly, the position of the substrate surface 21S in the first direction is defined, and thus the position of the projection 30 relative to the placement region Es is defined.

Further, the shoulder 52 may be provided on the entire inner periphery of the side wall 56 along the inner surface of the side wall 56, or may be provided intermittently along the inner surface of the side wall 56. Further, the positioning structure may be provided by a structure different from the shoulder 52 as long as positioning of the substrate surface 21S can be defined.

Further, the tray 50 and the cell transplantation device 10 preferably include a positioning structure that regulates a position of the projection 30 relative to a position of the placement region Es in the second direction, that is, in the direction perpendicular to the depth direction of the tray 50.

For example, an internal diameter of a portion of the side wall 56 closer to the opening of the tray 50 than the shoulder 52 is corresponds to an external diameter of the substrate 20. Accordingly, since the substrate 20 fits in the side wall 56, the position of the projection 30 relative to the placement region Es in the second direction is regulated. Further, when the tray 50 has a plurality of placement regions Es and the cell transplantation device 10 has a plurality of projections 30, the positioning structure in the second direction preferably includes a structure for aligning an arrangement orientation of the placement regions Es and an arrangement orientation of the projections 30.

Figure 34:
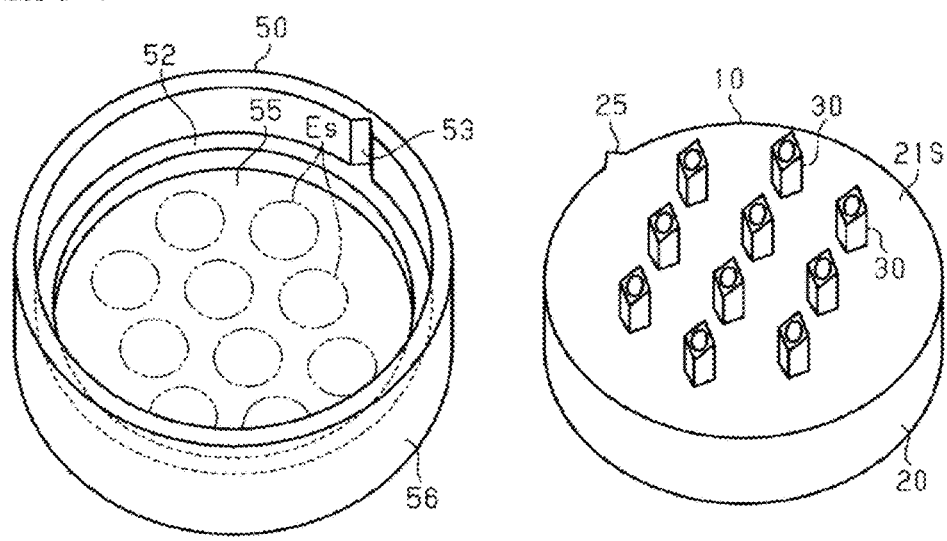
FIG. 34 is a view illustrating another example of a tray and a cell transplantation device in a cell transplantation unit of an embodiment.

Such a positioning structure includes, for example, as shown in FIG. 34, a groove 53 formed on the inner surface of the side wall 56 and a protrusion 25 formed on the outer surface of the substrate 20. The cell transplantation device 10 is inserted in the tray 50 so that the protrusion 25 fits in the groove 53. Here, positions of the groove 53 and the protrusion 25 are set so that each projection 30 faces a respective placement region Es. Accordingly, the arrangement orientation of the placement regions Es and the arrangement orientation of the projections 30 corresponds to each other, and the positions of the projections 30 relative to the positions of the placement regions Es in the second direction are regulated.

In addition, the amount and positions of the grooves 53 and the amount and positions of the protrusion 25 are not limited. Further, the tray 50 may include a protrusion, and the substrate 20 may include a groove. That is, the arrangement orientation of the placement regions Es and the arrangement orientation of the projections 30 may be aligned by fitting of the groove and the protrusion. In addition, the positioning structure may also be achieved by a structure different from the groove and the protrusion as long as the arrangement orientation of the placement regions Es and the arrangement orientation of the projections 30 can be aligned.

Figure 35:
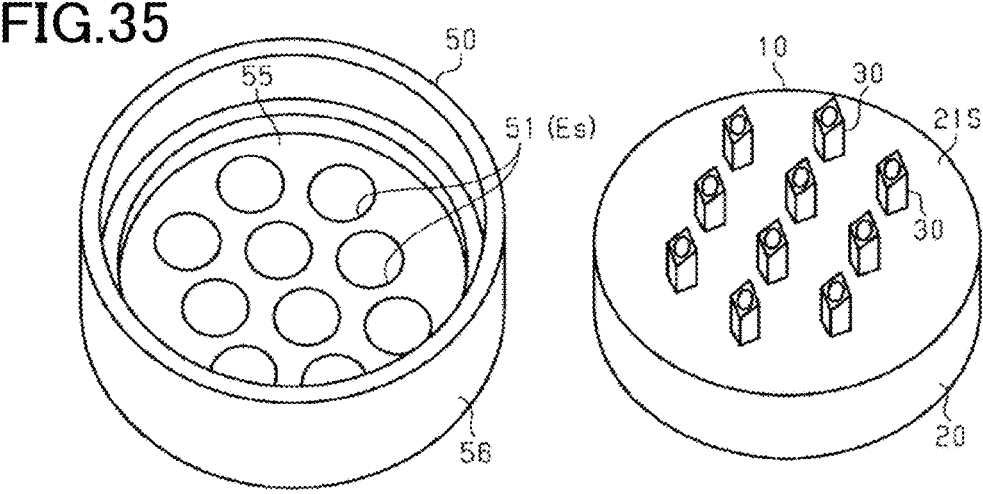
FIG. 35 is a view illustrating a perspective structure of another example of a tray and a cell transplantation device in a cell transplantation unit of an embodiment.
Figure 36:
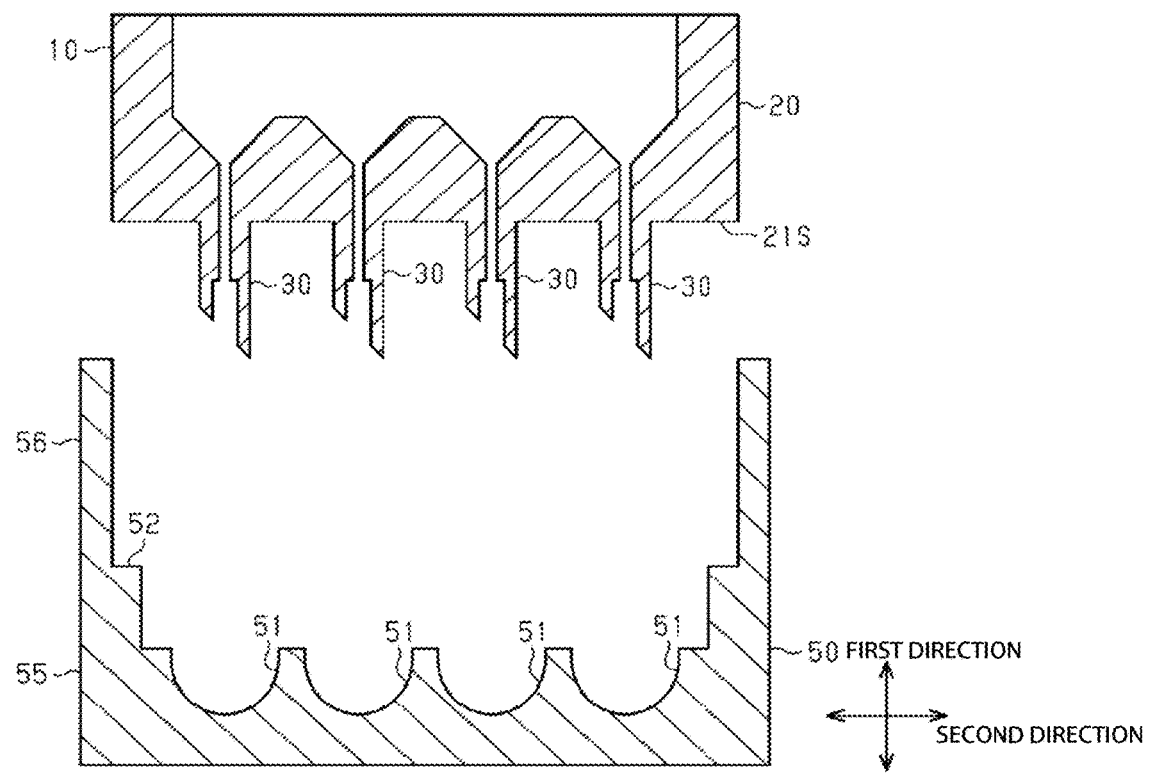
FIG. 36 is a view illustrating placement of another example of a tray and a cell transplantation device when an accommodating step is performed in a cell transplantation unit of an embodiment.

As shown in FIG. 35, the tray 50 may include one or more recesses 51 on the bottom 55, and the cell group and the protective liquid may be placed in the recess 51. In this case, each recess 51 is the placement region Es. As shown in FIG. 36, in which the placement region Es is the recess 51, each projection 30 is assigned to a respective recess 51, which is a respective placement region Es, such that the recess 51 and the projection 30 correspond to each other one to one. That is, when the tray 50 and the cell transplantation device 10 face each other in the first direction, each recess 51 face a respective projection 30.

Figure 37:
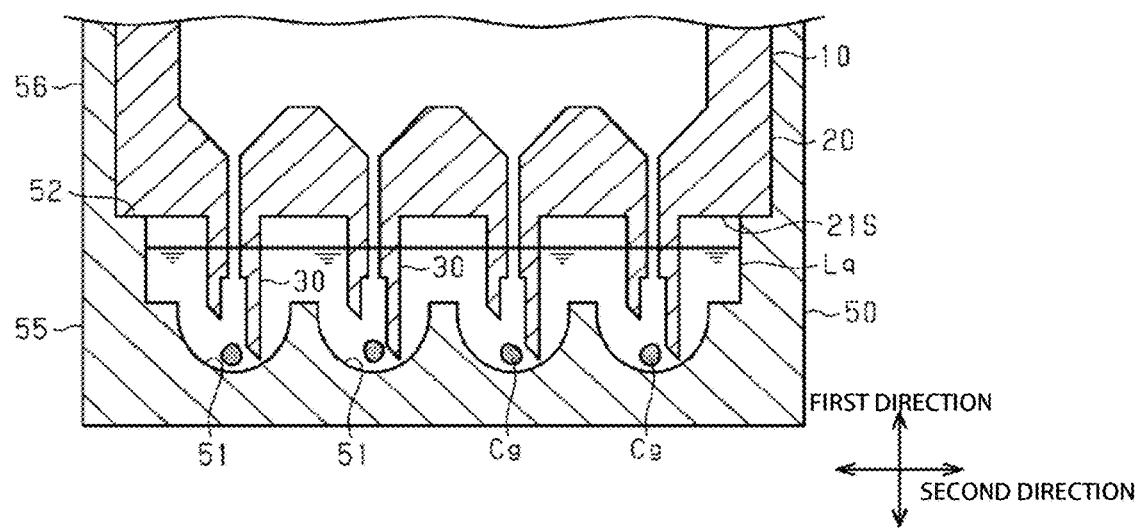
FIG. 37 is a view illustrating an accommodating step of cell groups by using a cell transplantation unit of an embodiment.

As shown in FIG. 37, in accommodation of the cell groups Cg into the cell transplantation device 10, the distal region of each projection 30 is inserted into a respective recess 51, and the cell group Cg together with the protective liquid Lq is taken into the projection 30 via the opening 32. When the placement region Es is the recess 51, the tray 50 and the cell transplantation device 10 also preferably include a positioning structure that regulates a position of the projection 30 relative to a position of the placement region Es in the first direction. For example, the positioning structure is composed of an end of the substrate surface 21S of the cell transplantation device 10, and the shoulder 52 provided along the inner surface of the side wall 56, and regulates the length of the projection 30 to be inserted in the recess 51 to a length suitable for taking in the cell groups Cg.

Further, when the placement region Es is the recess 51, the tray 50 and the cell transplantation device 10 also preferably include a positioning structure that regulates a position of the projection 30 relative to a position of the placement region Es in the second direction. For example, an internal diameter of a portion of the side wall 56 closer to the opening of the tray 50 than the shoulder 52 is corresponds to an external diameter of the substrate 20. Accordingly, since the substrate 20 fits in the side wall 56, the position of the projection 30 relative to the placement region Es in the second direction is regulated.

Figure 38:
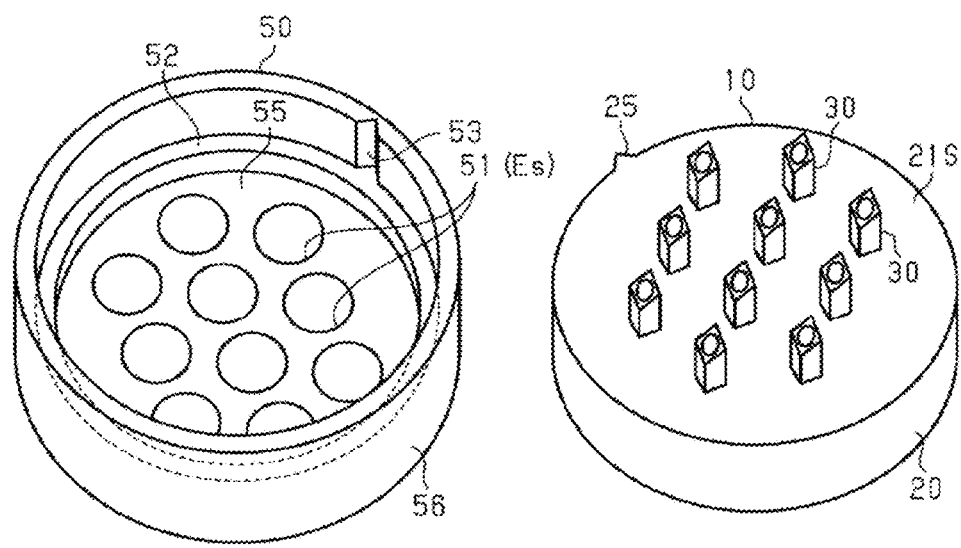
FIG. 38 is a view illustrating another example of a tray and a cell transplantation device in a cell transplantation unit of an embodiment.

Further, as shown in FIG. 38, when the tray 50 has a plurality of recesses 51 and the cell transplantation device 10 has a plurality of projections 30, the positioning structure in the second direction preferably includes a structure for aligning an arrangement orientation of the recesses 51 and an arrangement orientation of the projections 30. As shown in FIG. 38, such a positioning structure includes the groove 53 formed on the inner surface of the side wall 56 and a protrusion 25 formed on the outer surface of the substrate 20.

Alternatively, as previously shown in FIG. 5, the tray 50 may be configured to hold the cell group Cg and the protective liquid Lq inside and around the through hole 54 of the tray 50. In this case, the region inside and around the through hole 54 is the placement region Es. Regardless of the configuration of the placement region Es, each projection 30 may be assigned to a respective placement region Es in the cell transplantation unit. Further, the tray 50 and the cell transplantation device 10 preferably include a positioning structure that regulates a position of the projection 30 relative to a position of the placement region Es in both the first and second directions.

Figure 39:
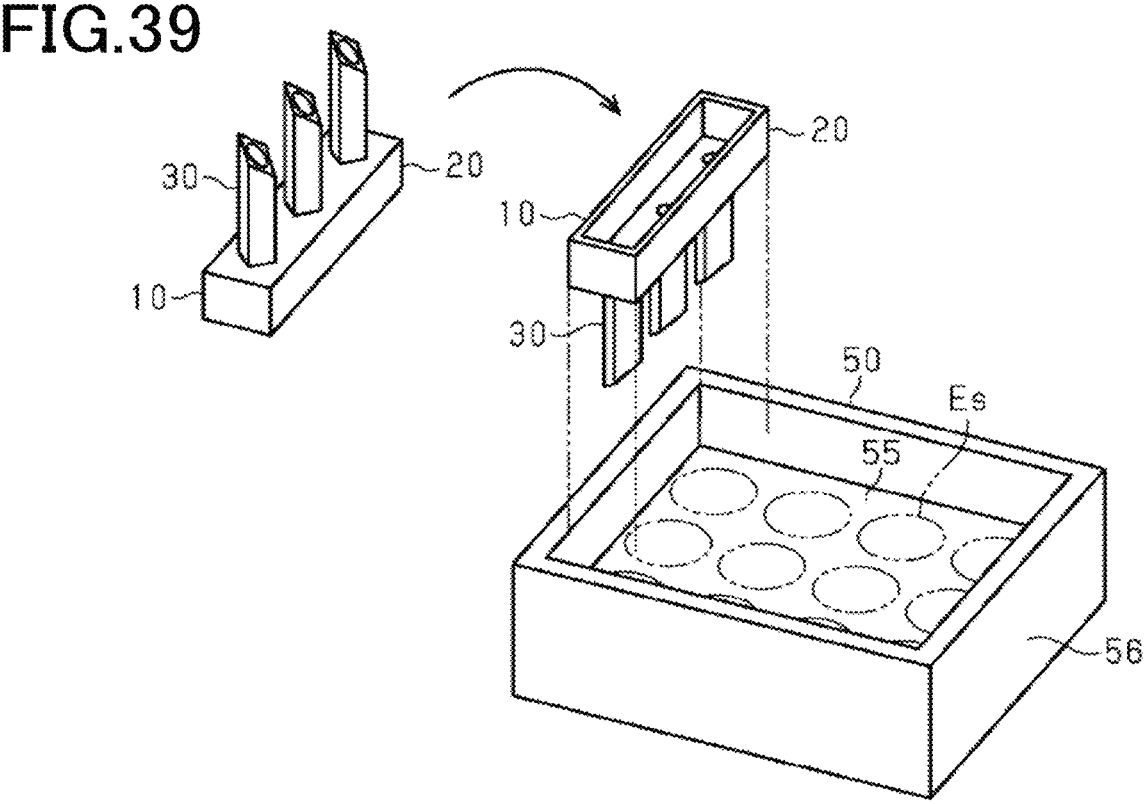
FIG. 39 is a view illustrating another example of a tray and a cell transplantation device in a cell transplantation unit of an embodiment.

In addition, when the placement regions Es of the amount and arrangement corresponding to the amount and arrangement of the projections 30 in the cell transplantation device 10 are regarded as one group, the tray 50 may include a plurality of groups of the placement regions Es. For example, as shown in FIG. 39, when the cell transplantation device 10 includes the projections 30 arranged in a line, the tray 50 may have a configuration having a plurality of groups of the placement regions Es arranged in a line. The amount and arrangement of the placement regions Es correspond to the amount and arrangement the projections 30 of the cell transplantation device 10. In such a configuration, accommodation of the cell groups Cg into the cell transplantation device 10 is repeated for each of the placement regions Es. That is, for one line of the placement regions Es, which is one group, the distal region of each projection 30 is directed to a respective placement region Es so that the cell groups Cg are taken into the respective projections 30. After the cell groups Cg that have been taken in are transplanted, accommodation of the cell groups Cg into the cell transplantation device 10 is repeated for the placement regions Es of another group. By shifting the target group in sequence, the cell groups Cg in the tray 50 are sequentially accommodated in the cell transplantation device 10 and transplanted.

Figure 40:
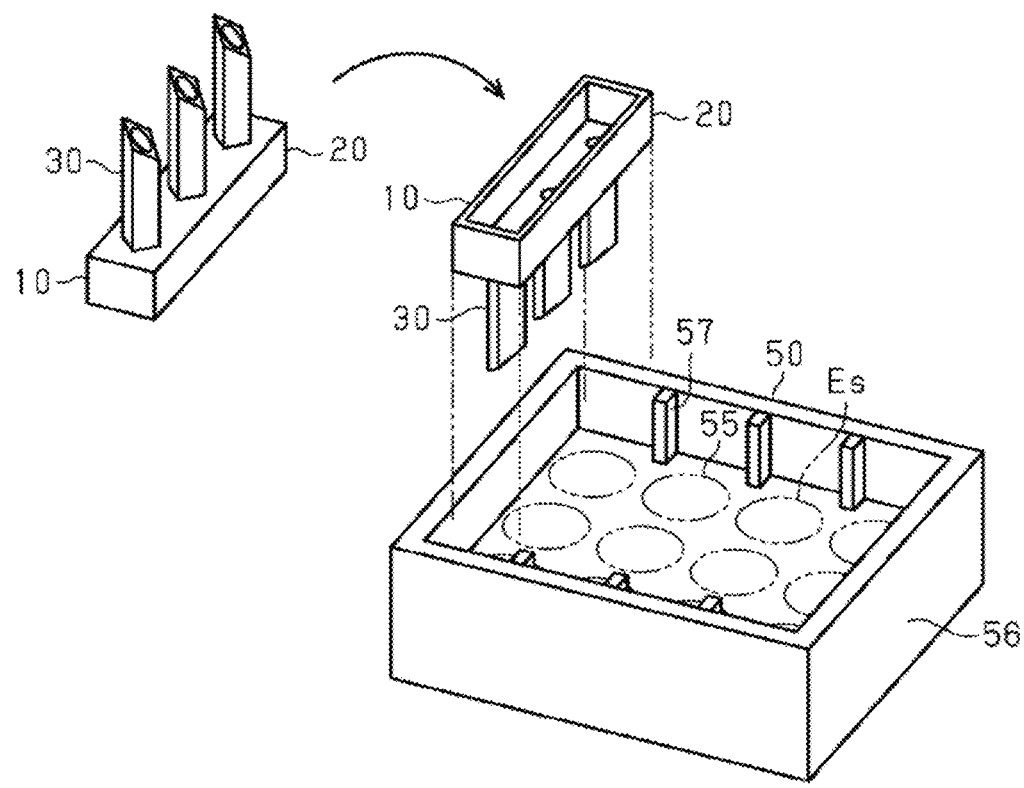
FIG. 40 is a view illustrating another example of a tray and a cell transplantation device in a cell transplantation unit of an embodiment.

As described above, when the tray 50 includes the placement regions Es of the amount and arrangement corresponding to the amount and arrangement of the projections 30 in the cell transplantation device 10, it can also be regarded that each projection 30 is assigned to a respective placement region Es. In this case as well, the tray 50 and the cell transplantation device 10 preferably include a positioning structure that regulates a position of the projection 30 relative to a position of the placement region Es in both the first and second directions. For example, FIG. 40 illustrates a form in which the tray 50 includes a partition 57 protruding from the inner surface of the side wall 56 as a positioning structure that regulates the position of the projection 30 relative to the position of the placement region Es in the second direction. The partition 57 is located at the boundary between the groups of the placement regions Es adjacent to each other. When the cell transplantation device 10 fits in a region partitioned by the partition 57, the position of the projection 30 relative to the position of the placement region Es is regulated in the second direction, and the placement regions Es and the projections 30 in one group face each other. In each group, the arrangement orientation of the placement regions Es and the arrangement orientation of the projections 30 are aligned with each other.

As described above, according to the cell transplantation device and the cell transplantation unit of the present embodiment, the following effects can be achieved.

(1) Since the cell transplantation device 10 includes the accommodating portion and the penetrating portion, penetration of the penetrating portion into a target region and release of a cell group accommodated in the accommodating portion through the opening can be continuously performed by a single device. Therefore, cells can be smoothly transplanted.

(2) When the cell transplantation device 10 has a configuration having the placement assisting portion, placement of the cell groups in the target region is assisted, and thus cell groups can be smoothly placed in the target region.

(3) When the projection 30 functions as the accommodating portion and the penetrating portion, the accommodating portion and the opening 32 of the penetrating portion can be provided at closer positions compared with a case where the accommodating portion and the penetrating portion are separate structures. Accordingly, it is possible to reduce time, effort, and the like required to transfer a cell group from the accommodating portion to the opening 32 to thereby reduce a load required for the transfer of a cell group. Further, by adjusting the amount of cell groups to be accommodated in the projection 30, the amount of cell groups to be placed in the target region by one projection 30 can be adjusted.

(4) In the form in which the cell groups are taken in via the opening 32 of the projection 30, the opening 32 functions as the outlet and intake of the cell group. Accordingly, compared with a case where an outlet and an intake are separately provided in the projection 30, the projection 30 has a simple structure. Further, compared with a case where the structure having an intake is separately provided from the projection 30, the accommodating portion and the intake can be provided at closer positions to each other. Accordingly, it is possible to reduce time, energy, and the like required to transfer a cell group from the intake to the accommodating portion to thereby reduce a load required for the transfer of a cell group.

(5) In the form in which the cell groups are taken into the projection 30 by using at least one of capillary phenomenon, suction, and electroosmotic flow, in particular, by using suction, the cell groups can be suitably taken into the projection 30. Further, when the cell transplantation device 10 includes a plurality of projections 30, the cell groups can be collectively accommodated in the plurality of projections 30. Accordingly, accommodation efficiency of cell groups can be increased.

(6) In the configuration in which the cell transplantation device 10 includes a plurality of projections 30, a plurality of cell groups can be collectively placed in the target region. Accordingly, compared with a case where cell groups are transferred one by one, repeated operations in cell transplantation are reduced. Thus, cells can be more smoothly transplanted.

(7) In the configuration in which each of the plurality of projections 30 has a structure that accommodates cell groups of a predetermined amount, it is possible to reduce variation in the amount of placed cell groups depending on the positions in the site where the cell groups are transplanted. That is, in the direction parallel to the skin surface, uniform placement of the cell groups is easily performed.

(8) In the configuration in which the internal channel 31 has the large diameter portion 33 having the opening 32, and the small diameter portion 34 that communicates with the large diameter portion 33 has a cross-sectional area of flow path smaller than that of the large diameter portion 33, the cell group can be easily held by the large diameter portion 33. Accordingly, the cell groups taken into the internal channel 31 through the opening 32 can be easily retained in the projection 30.

(9) The cell group to be transplanted is a cell group that contributes to hair growth or hair restoration, and specifically, a hair follicle primordium. By using the cell transplantation device 10 that places the cell groups in a target region, which is at least one of the intradermal layer and subcutaneous layer, accurate transplantation of the cell groups can be performed. For the purposes of hair growth or hair restoration, it is often required to transplant an amount of the aforementioned cell groups. Using the cell transplantation device 10 described above for transplantation of these cell groups greatly improves the efficiency of cell transplantation, which is a great advantage for smooth cell transplantation.

(10) In the cell transplantation unit, since each accommodating portion is assigned to a respective placement region Es, it is possible to easily set the amount of cell groups accommodated in the accommodating portion. It is also possible to accommodate a predetermined amount of cell groups in the respective projections 30.

(11) When the cell transplantation unit has a configuration in which the position of the projection 30 relative to the position of the placement region Es is regulated in the depth direction of the tray 50, the position of the projection 30, in accommodation of cell groups, can be easily aligned with the placement region Es. Further, when the cell transplantation unit has a configuration in which the position of the projection 30 relative to the position of the placement region Es is regulated in a direction perpendicular to the depth direction of the tray 50, the position of the projection 30, in accommodation of cell groups, can be easily aligned with the placement region Es in the direction perpendicular to the depth direction of the tray 50.

(12) In the configuration in which the tray 50 in the cell transplantation unit is a culture container used for culture of cell groups, transplantation is completed when cell groups are transferred to the target region from the container in which the cell groups have been cultured. Accordingly, compared with the form in which cell groups are transferred from the culture container to a tray separately provided from the culture container and then accommodated in the cell transplantation device 10 from the tray to be placed in the target region, it is possible to reduce the number of operations required for transplantation, and thus improve transplantation efficiency.

Modifications

The above embodiments can be performed with the following modifications.

The cell group to be transplanted may not be necessarily a cell group that contributes to hair growth or hair restoration, and may be any cell group that exhibits desired effects when placed in the intradermal or subcutaneous layer. For example, the cell group to be transplanted may be a cell group that exhibits effects in cosmetic use such as elimination of wrinkles or improvement in moisturizing state in the skin. In the above embodiment, a configuration other than the configuration which has been described as a suitable configuration when the cells to be transplanted is a hair follicle primordium, for example, a configuration for accommodating cell groups into the accommodating portion, a configuration for the shape of the penetrating portion, and a configuration of the placement assisting portion, can achieve the same effects as those described in the above embodiments even if the cell group to be transplanted is different from the cell group that contributes to hair growth or hair restoration.

The present application addresses the following. Cells are cultured in a culture container in which a medium is contained. For smooth transplantation of cells into a living body, it is desired to smoothly transfer the cells from a culture container to a skin region in the living body. For example, in a transplantation method in which an incision is made in a transplantation site in the skin with a scalpel, and then cell groups in a culture container are picked one by one with tweezers or the like and transferred to an intradermal site, it is required to frequently repeat operations of exchanging the tools used and transferring cell groups, which may hinder smooth transplantation. While research and development on cell culturing have been actively conducted as described above, there have been a few reports of research and development focusing on cell transplantation. Accordingly, proposals for tools and methods for smooth cell transplantation are still desired.

The present invention has an aspect to provide a cell transplantation device and a cell transplantation unit capable of smooth transplantation of cells.

A cell transplantation device is a cell transplantation device for placing a cell group into a target region, which is at least one of the intradermal layer and subcutaneous layer in a living body, the cell transplantation device includes: an accommodating portion that accommodates a liquid material containing the cell group; and a penetrating portion having an opening that communicates with the accommodating portion, the penetrating portion being configured to be advanced toward the target region via a skin surface of the living body so that the opening is placed at the target region.

With this configuration, the accommodating portion and the penetrating portion are provided in a single device. Accordingly, penetration of the penetrating portion into a target region and release of a cell group accommodated in the accommodating portion through the opening can be continuously performed by a single device. Therefore, cells can be smoothly transplanted.

In the above configuration, the cell transplantation device may further include a placement assisting portion that assists placement of the cell group into the target region.

With this configuration, since placement of the cell groups in the target region is assisted, cell groups can be smoothly placed in the target region.

In the above configuration, the cell transplantation device may include: a substrate having a substrate surface; and a projection protruding from the substrate surface and functioning as the accommodating portion and the penetrating portion, wherein the projection may be a structure having the opening and a channel inside the projection, the channel extending from the opening.

With this configuration, the projection functions as the accommodating portion and the penetrating portion. Accordingly, compared with a case where the accommodating portion and the penetrating portion are separate structures, the accommodating portion and the opening of the penetrating portion can be provided at closer positions. Accordingly, it is possible to reduce time, energy, and the like required to transfer a cell group from the accommodating portion to the opening to thereby reduce a load required for the transfer of a cell group.

In the above configuration, the cell transplantation device may be configured to take the cell group into the channel through the opening of the projection.

With this configuration, the opening functions as an outlet and an intake for cell groups. Accordingly, compared with a case where an outlet and an intake are separately provided in the projection, the projection has a simple structure. Further, compared with a case where the structure having an intake is separately provided from the projection, the accommodating portion and the intake can be provided at closer positions. Accordingly, it is possible to reduce time, energy, and the like required to transfer a cell group from the intake to the accommodating portion to thereby reduce a load required for the transfer of a cell group.

In the above configuration, the cell transplantation device may be configured to take the cell group into the channel by suctioning the liquid material.

With this configuration, cell groups can be suitably taken into the projection. Further, when the cell transplantation device includes a plurality of projections, cell groups can be collectively accommodated in the plurality of projections. Accordingly, accommodation efficiency of cell groups can be increased.

In the above configuration, the cell transplantation device may include a plurality of the projections.

With this configuration, a plurality of cell groups can be collectively placed in the target region. Accordingly, compared with a case where cell groups are transferred one by one, repeated operations in cell transplantation are reduced. Thus, cells can be more smoothly transplanted.

In the above configuration, the cell group may be an aggregate of cells, and each projection may have a structure that accommodates a predetermined amount of the cell groups.

With this configuration, it is possible to reduce variation in the amount of placed cell groups depending on the positions in the site where the cell groups are transplanted.

In the above configuration, the channel may have a first portion which includes the opening, and a second portion communicating with the first portion and having a cross-sectional flow path area smaller than that of the first portion.

With this configuration, cell groups are less likely to pass through the second portion than the first portion, and tend to be held in the first portion. Accordingly, cell groups taken into the channel through the opening can be easily retained in the projection.

In the above configuration, a portion of the projection which functions as the penetrating portion may have a length in a range of 200 μm or more and 6 mm or less. With this configuration, it is possible to achieve a penetrating portion having a length suitable for placing the opening at the target region, which is at least one of the intradermal layer and subcutaneous layer.

In the above configuration, the substrate surface may have an area in a range of 0.005 $cm^2$ or more and 4 $cm^2$ or less.

With this configuration, when a site where cell groups are transplanted is the scalp, the substrate surface can easily follow the scalp, since the extending area of the substrate surface is not too large to follow a curvature of the scalp. Therefore, the projection is capable of piercing the skin to a sufficient depth.

In the above configuration, the opening may have an opening area in a range of 5000 $μm^2$ or more and 300000 $μm^2$ or less.

With this configuration, it is possible to achieve the opening having a size suitable for hair follicle primordia, as a cell group, entering or exiting the opening.

In the above configuration, the cell transplantation device may be a device for placing a cell group that contributes to hair growth or hair restoration as the cell group into the target region. In the above configuration, the cell transplantation device may be a device for placing hair follicle primordia as the cell group into the target region.

With this configuration, accurate transplantation of the cell groups can be performed by using the cell transplantation device that places the cell groups in a target region, which is at least one of the intradermal layer and subcutaneous layer. For the purposes of hair growth or hair restoration, it is often required to transplant an amount of the aforementioned cell groups. Using the cell transplantation device described above for transplantation of these cell groups greatly improves the efficiency of cell transplantation, which is a great advantage for smooth cell transplantation.

A cell transplantation unit for solving the above problem is a cell transplantation unit including: a tray having at least one placement region, which is a region where a cell group is to be placed; and a cell transplantation device configured to transfer the cell group from the tray to a target region, which is at least one of the intradermal layer and subcutaneous layer in a living body, wherein the cell transplantation device includes: at least one accommodating portion for taking in a liquid material containing the cell group from the placement region, each accommodating portion being assigned to a respective placement region; and a penetrating portion having an opening that communicates with the accommodating portion, the penetrating portion being configured to be advanced toward the target region via a skin surface of the living body so that the opening is placed at the target region.

With this configuration, since each accommodating portion is assigned to a respective placement region, it is possible to easily set the amount of cell groups accommodated in the accommodating portion. It is also possible to accommodate a predetermined amount of cell groups in the respective projections. Further, penetration of the penetrating portion into a target region and release of a cell group accommodated in the accommodating portion through the opening can be continuously performed by a single device. Accordingly, cells can be smoothly transplanted.

In the above configuration, the cell transplantation device may include: a substrate having a substrate surface; and a projection protruding from the substrate surface and functioning as the accommodating portion and the penetrating portion, wherein the projection may be a structure having the opening and a channel inside the projection, the channel extending from the opening, and the tray and the cell transplantation device may have a structure that regulates a position of the projection relative to a position of the placement region in a depth direction of the tray.

With this configuration, the position of the projection relative to the position of the placement region is regulated in the depth direction of the tray. Accordingly, in accommodation of cell groups, the position of the projection can be easily aligned with the placement region.

In the above configuration, the cell transplantation device may include: a substrate having a substrate surface; and a projection protruding from the substrate surface and functioning as the accommodating portion and the penetrating portion, wherein the projection may be a structure having the opening and a channel inside the projection, the channel extending from the opening, and the tray and the cell transplantation device may have a structure that regulates a position of the projection relative to a position of the placement region in a direction perpendicular to a depth direction of the tray.

With this configuration, the position of the projection relative to the position of the placement region is regulated in a direction perpendicular to the depth direction of the tray. Accordingly, in accommodation of cell groups, the position of the projection can be easily aligned with the placement region.

In the above configuration, the tray may be a culture container for use in culturing of the cell group.

With this configuration, transplantation is completed when cell groups are transferred to the target region from the container in which the cell groups have been cultured. Accordingly, compared with a case where cell groups are transferred from the culture container to a tray separately provided from the culture container, it is possible to reduce operation required for transplantation, and thus improve transplantation efficiency.

According to embodiments of the present invention, cells can be smoothly transplanted.

REFERENCE SIGNS LIST

Es . . . placement region
Cg . . . cell group
Lh . . . storage liquid
Lq . . . protective liquid
10 . . . cell transplantation device
20 . . . substrate
21S substrate surface
22 . . . proximal flow path
23 . . . intermediate flow path
24 . . . common flow path
25 . . . protrusion
30 . . . projection
31 internal channel
32 . . . opening
33 . . . large diameter portion
34 . . . small diameter portion
35S . . . side surface
36S . . . top surface
40 . . . induction unit
41 . . . pressurizing unit
42 . . . penetration assistance member
43 . . . positional adjustment unit
44 . . . elastic body
45 support portion
46 . . . insertion portion
47, 48 . . . penetration control unit
50 . . . tray
51 . . . recess
52 . . . shoulder
53 . . . groove
54 . . . through hole
55 . . . bottom surface
56 . . . side wall
57 partition Obviously, numerous modifications and variations of the present invention are possible in light of the above teachings. It is therefore to be understood that within the scope of the appended claims, the invention may be practiced otherwise than as specifically described herein.

What is claimed is:

1. A cell transplantation device for placing a cell group at a target region in at least one of an intradermal layer and a subcutaneous layer in a living body, comprising:
a device body including a protruding portion comprising at least one projection such that the at least one projection has an internal channel configured to accommodate a liquid composition including the cell group and that the internal channel has a first portion and a second portion communicating with the first portion and having a cross-sectional flow path area that is smaller than a cross-sectional flow path area of the first portion,
wherein the protruding portion has an opening formed in the first portion of the internal channel and communicating with the internal channel, and the protruding portion is configured to penetrate a skin surface of the living body such that the opening of the protruding portion reaches the at least one of the intradermal layer and the subcutaneous layer and that the cell group accommodated in the internal channel is placed at the target region through the opening.

2. The cell transplantation device according to claim 1, further comprising:
a placement assisting device configured to apply a pressure such that the cell group is placed at the target region.

3. The cell transplantation device according to claim 1, wherein the device body includes a substrate having a substrate surface such that the comprises at least one projection is formed on the substrate surface.

4. The cell transplantation device according to claim 3, wherein the internal channel is extended from the opening such that the cell group is movable into the internal channel through the opening.

5. The cell transplantation device according to claim 3, wherein the internal channel is extended from the opening such that the cell group is movable into the internal channel through the opening by suctioning the liquid composition.

6. The cell transplantation device according claim 5, wherein the at least one projection comprises a plurality of projections.

7. The cell transplantation device according to claim 6, wherein the cell group is an aggregate including a plurality of cells, and each of the projections is configured to accommodate a predetermined amount of cells.

8. The cell transplantation device according to claim 6, wherein the substrate has a plurality of proximal flow paths extending from the substrate surface and connected to the plurality of projections respectively, a plurality of intermediate flow paths connecting to the proximal flow paths respectively and each having an internal diameter gradually increasing from a respective one of the proximal flow paths toward an end away from the substrate surface, and a common flow path communicating with the plurality of intermediate flow paths.

9. The cell transplantation device according claim 3, wherein the at least one projection comprises a plurality of projections.

10. The cell transplantation device according to claim 9, wherein the cell group is an aggregate including a plurality of cells, and each of the projections is configured to accommodate a predetermined amount of cells.

11. The cell transplantation device according to claim 10, wherein the substrate has a plurality of proximal flow paths extending from the substrate surface and connected to the plurality of projections respectively, a plurality of intermediate flow paths connecting to the proximal flow paths respectively and each having an internal diameter gradually increasing from a respective one of the proximal flow paths toward an end away from the substrate surface, and a common flow path communicating with the plurality of intermediate flow paths.

12. The cell transplantation device according to claim 9, wherein the substrate has a plurality of proximal flow paths extending from the substrate surface and connected to the plurality of projections respectively, a plurality of intermediate flow paths connecting to the proximal flow paths respectively and each having an internal diameter gradually increasing from a respective one of the proximal flow paths toward an end away from the substrate surface, and a common flow path communicating with the plurality of intermediate flow paths.

13. The cell transplantation device according to claim 3, wherein the at least one projection is configured to penetrate the skin surface and has a length in a range of 200 μm to 6 mm.

14. The cell transplantation device according to claim 3, wherein the substrate surface has an area in a range of 0.005 cm$^2$ to 4 cm$^2$.

15. The cell transplantation device according to claim 3, wherein the opening has an opening area in a range of 5000 μm$^2$ to 300000 μm$^2$.

16. A hair growth or hair restoration method, comprising:
accommodating a liquid composition including a cell group comprising hair follicle primordia in the cell transportation device of claim 1; and
transporting the cell group from the at least one projection in the cell transportation device to the target region in the living body.

17. A cell transplantation apparatus, comprising:
a tray having at least one placement region such that the at least one placement region is configured to hold a liquid composition including a cell group; and
a cell transplantation device configured to transfer the cell group from the tray to a target region in at least one of an intradermal layer and a subcutaneous layer in a living body and comprising a device body including a protruding portion comprising at least one projection such that the at least one projection has an internal channel configured to accommodate the liquid composition including the cell group and that the internal channel has a first portion and a second portion communicating with the first portion and having a cross-sectional flow path area that is smaller than a cross-sectional flow path area of the first portion,
wherein the internal channel is respectively assigned to the at least one placement region, the protruding portion has an opening formed in the first portion of the internal channel and communicating with the internal channel, and the protruding portion is configured to penetrate a skin surface of the living body such that the opening of the protruding portion reaches the at least one of the intradermal layer and the subcutaneous layer and that the cell group accommodated in the internal channel is placed at the target region through the opening.

18. The cell transplantation apparatus according to claim 17, wherein the device body includes a substrate having a substrate surface, such that the at least one projection is formed on the substrate surface, and the tray and the cell transplantation device are configured to control a position of the at least one projection relative to a position of the at least one placement region in a depth direction of the tray.

19. The cell transplantation apparatus according to claim 17, wherein the device body includes a substrate having a substrate surface such that the at least one projection is formed on the substrate surface, and the tray and the cell transplantation device are configured to control a position of the at least one projection relative to a position of the at least one placement region in a direction perpendicular to a depth direction of the tray.

20. The cell transplantation apparatus according to claim 17, wherein the tray is a culture container configured to culture the cell group.

* * * * *